US007033753B1

(12) United States Patent
Kool

(10) Patent No.: US 7,033,753 B1
(45) Date of Patent: Apr. 25, 2006

(54) COMPOSITIONS AND METHODS FOR NONENZYMATIC LIGATION OF OLIGONUCLEOTIDES AND DETECTION OF GENETIC POLYMORPHISMS

(75) Inventor: Eric T. Kool, Stanford, CA (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/483,337

(22) Filed: Jan. 14, 2000

Related U.S. Application Data

(60) Provisional application No. 60/116,059, filed on Jan. 15, 1999.

(51) Int. Cl.
*C07H 21/00* (2006.01)
*C12Q 1/68* (2006.01)
(52) U.S. Cl. .................. 435/6; 536/23.1; 536/24.5; 536/24.3
(58) Field of Classification Search ............... 536/23.1, 536/26.7, 26.8, 27.3, 27.7, 27.81, 28.5, 28.53, 536/25.33, 26.5, 26.6, 24.3, 24.5; 435/6
See application file for complete search history.

(56) References Cited

U.S. PATENT DOCUMENTS

| 5,476,930 A | 12/1995 | Letsinger et al. ........... 536/25.3 |
| 5,571,903 A | 11/1996 | Gryaznov ................... 536/23.1 |
| 5,681,943 A | 10/1997 | Letsinger et al. ........ 536/25.33 |
| 5,688,641 A | 11/1997 | Sager et al. |
| 5,707,804 A | 1/1998 | Mathies et al. ................. 435/6 |
| 5,714,320 A | 2/1998 | Kool ............................. 435/6 |
| 5,780,613 A | 7/1998 | Letsinger et al. ........ 536/25.33 |
| 6,020,483 A | 2/2000 | Beckvermit et al. |
| 6,090,932 A | 7/2000 | McGee et al. |
| 6,111,086 A | 8/2000 | Scaringe |
| 2004/0259102 A1 | 12/2004 | Kool |

FOREIGN PATENT DOCUMENTS

| WO | WO 94/24143 | 10/1994 |
| WO | WO 96/35699 | 11/1996 |
| WO | WO 97/05284 | 2/1997 |
| WO | WO 97/22719 | 6/1997 |
| WO | WO 97/43298 | 11/1997 |
| WO | WO 98/04746 | 2/1998 |
| WO | WO 98/38296 | 9/1998 |

OTHER PUBLICATIONS

King et al., *A Dictionary of Genetics*, Oxford University Press, New York, NY, 1985, only pp. 155, 156 and 304 supplied.*
King et al. (I), *A Dictionary of Genetics*, Oxford University Press, New York, NY, 1985, only pp. 155, 156 and 304 supplied.*
Sommer et al., "Minimal Homology for PCR Primers," *Nucleic Acids Research*, 17(16), 6749 (1989).*
King et al. (II), *A Dictionary of Genetics*, Oxford University Press, New York, NY, 1985, only pp. 255, 307 and 416 supplied.*
Lehninger, A., *Biochemistry*, Second Edition, Worth Publishers, Inc., Mew York, NY, Jul., 1978, only pp. 898-899 supplied.*
King et al. (I), A Dictionary of Genetics, Oxford University Press, New York, NY, 1985, only pp. 155, 156 and 304 supplied.*
Sommer et al., "Minimal Homology for PCR Primers," Nucleic Acids Research, 17(16), 6749 (1989).*
King et al. (II), A Dictionary of Genetics, Oxford University Press, New York, NY, 1985, only pp. 255, 307 and 416 supplied.*
Lehninger, A., Biochemistry, Second Edition, Worth Publishers, Inc., New York, NY, Jul., 1978, only pp. 898-899 supplied.*
Lehninger, A., *Biochemistry*, Second Edition, Worth Publishers, Inc., Mew York, NY, Jul., 1978, only pp. 898-899 supplied.*
Rychlik et al., "Optimization of the Annealing Temperature for DNA in vivo," Nucleic Acids Research, 18(21), 6409-6412 (Nov. 11, 1990).*
Beaucage et al., "Tetrahedron Report No. 309: Advances in the Synthesis of Oligonucleotides by the Phosphoramidite Approach," *Tetrahedron*, 48(12):2223-2311 (1992), month not available.
Cook, "Nucleoside S-Alkyl Phosphorothioates. IV. Synthesis of Nucleoside Phosphorothioate Monoesters," *J. Am. Chem. Soc.*, 92(1):190-195 (Jan. 14, 1970).
Gamper et al., "Solution Hybridization of Crosslinkable DNA Oligonucleotides to Bacteriophage M13 DNA," *J. Mol. Biol.*, 197:349-362 (1987), month not available.
Gryaznov et al., "Chemical Ligation of Oligonucleotides in the Presence and Absence of a Template," *J. Am. Chem Soc.*, *115* (9):3808-3809 (May 5, 1993).
Gryaznov et al., "Template controlled coupling and recombination of oligonucleotide blocks containing thiophosphoryl groups," *Nuc. Acids Res., 21* (6):1403-1408 (Mar. 25, 1993).
Gryaznov et al., "Enhancement of selectivity in recognition of nucleic acids via chemical autoligation," *Nuc. Acids Res.*, 22 (12):2366-2369 Jun. 25, 1994.
Herrlein et al., "A Covalent Lock for Self-Assembled Oligonucleotide Conjugates," *J. Am. Chem. Soc., 117* (40): 10151-10152 (1995), month not available.

(Continued)

*Primary Examiner*—L. E. Crane
(74) *Attorney, Agent, or Firm*—Mueting, Raasch & Gebhardt, P.A.

(57) ABSTRACT

The invention is directed to novel compositions and methods for nonenzymatic ligation of oligonucleotides. In one aspect of the invention, the nonenzymatic ligation is selenium-mediated or tellurium mediated ligation. In another aspect, the invention provides for the use of fluorescence resonance energy transfer (FRET) to detect the nonenzymatic ligation.

7 Claims, 19 Drawing Sheets

OTHER PUBLICATIONS

Herrlein et al., "Stability and Conformational Switching in a Mini-Cyclic Oligonucleotide Conjugate," *Angewandte Chemia, International Edition* 36 (6):599-601 (Apr. 4, 1997.)

Higgins et al., "[4] DNA-Joining Enzymes: A Review," *Methods in Enzymology, vol. 68, Recombinant DNA*, Wu, ed., Academic Press, New York, Title page, publication page and pp. 50-71 (1979), month not available.

Horn et al., "A Chemical 5'-Phosphorylation of Oligodeoxyribonucleotides That Can be Monitored by Trityl Cation Release," *Tetrahedron Lett.*, 27 (39):4705-4708 (1986), month not available.

Hung et al., "Optimization of Spectroscopic and Electrophoretic Properties of Energy Transfer Primers," *Anal. Biochem.*, 252 (1):78-88 Oct. 1, 1997.

Knight et al., "Phosphorylated Thiosugars: Synthesis, Properties, and Reactivity in Enzymatic Reactions," *Biochemistry*, 30 (20):4970-4977 (1991), month not available.

Landegren et al., "A Ligase-Mediated Gene Detection Technique," *Science*, 241:1077-1080 (Aug. 26, 1988).

Mag et al., "Synthesis and selective cleavage of an oligodeoxynucleotide containing a bridged internucleotide 5'-phosphorothioate linkage," *Nuc. Acids Res.*, 19(7):1437-1441 (1991), month not available.

Mori et al., "Phosphoroselenoate oligodeoxynucleotides: synthesis, physico-chemical characterization, anti-sense inhibitory properties and anti-HIV activity," *Nuc. Acids Res.*, 17(20):8207-8219 (1989), month not available.

Nilsson et al., "Padlock Probes: Circularizing Oligonucleotides for Localized DNA Detection," *Science*, 265:2085-2088 (Sep. 30, 1994).

Paris et al., "Probes DNA sequences in solution with a monomer-excimer fluorescence color change," *Nuc. Acids Res.*, 26(16):3789-3793 (1998), month not available.

Pritchard et al., "Effects of base mismatches on joining of short oligodeoxynucleotides by DNA ligases," *Nuc. Acids Res.*, 25(17):3403-3407 (1997), month not available.

Reddy et al., "A point mutation is responsible for the acquisition of transforming properties by the T24 human bladder carcinoma oncogene" *Nature* 300:149-152 Nov. 11, 1982.

Rybakov et al., "Some substrate properties of analogues of oligothymidylates with p-s-$C^{5'}$ bonds," *Nuc, Acids Res.*, 9(1):189-201 (1981), month not available.

Samiotaki et al., "Dual-Color Detection of DNA Sequence Variants by Ligase-Mediated Analysis," *Genomics*, 20(2):238-242 (Mar. 15, 1994), month not available.

Seeman, "DNA Nanotechnology: Novel DNA Constructions," *Annu. Rev. Biophys. Biomol. Struct.*, 27:225-248 (1998), month not available.

Somers et al., "Exonuclease enhances hybridization efficiency: Improved direct cycle sequencing and point mutation detection," *Biochim. Biophys. Acta*, 1379:42-52 (1998), month not available.

Stec et al., "Automated Solid-Phase Synthesis, Separation, and Stereochemistry of Phosphorothioate Analogues of Oligodeoxyribonucleotides," *J. Am. Chem. Soc.*, 106:6077-6079 (1984), month not available.

Usón et al., "Advances in direct methods for protein crystallography," *Curr. Opin. Struct. Biol.*, 9(5):643-648 (Oct., 1999).

van Tol et al., "Two autolytic processing reactions of a satellite RNA proceed with inversion of configuration," *Nuc. Acids Res.*, 18(8):1971-1975 (1990), month not available.

Verheyden et al., "Halo Sugar Nucleosides. I. Iodination of the Primary Hydroxyl Groups of Nucleosides with Methyltriphenoxyphosphonium Iodide," *J. Org. Chem.*, 35 (7):2319-2326 (1970), month not available.

Vu et al., "Internucleotide Phosphite Sulfurization with Tetraethylthiuram Disulfide. Phosphorothioate Oligonucleotide Synthesis Via Phosphoramidite Chemistry," *Tetrahedron Lett.*, 32(26):3005-3008 (1991), month not available.

Wang et al., "Relative stabilities of triple helices composed of combinations of DNA, RNA and 2'-O-methly-RNA backbones: chimeric circular oligonucleotides as probes," *Nuc. Acids Res.*, 23(7):1157-1164 (1995), month not available.

Xu et al., "A Novel 5'-Iodonucleoside Allows Efficient Nonenzymatic Ligation of Single-stranded and Duplex DNAs," *Tetrahedron Lett.*, 38(32):5595-5598 Aug. 11, 1997.

Xu et al., "Chemical and enzymatic properties of bridging 5'-S-phosphorthioester linkages in DNA," *Nuc. Acids Res.*, 26(13):3159-314 Jul. 1, 1998.

Xu et al., "High sequnce fidelity in a non-enzymatic DNA autoligation reaction," *Nuc. Acids Res.*, 27(3):875-881 (Feb. 1, 1999).

Xu, *Molecular Recognition and Detection of Nucleic Acid Sequences I. Sequence Specific Recognition of DNA by Circular Oligonucleotides II. A Novel DNA Autoligation Method Allowing Efficient Detection of Point Mutations*, Doctoral Thesis, Department of Chemistry, University of Rochester, Rochester, New York (1999), month not available.

March, "Chapter Ten-Aliphatic Nucleophilic Substitution," *Advanced Organic Chemistry: Reactions, Mechanisms, and Structure*, McGraw-Hill Book Company, 1968, pp. 251-375, month not available.

Sambrook and Russell, "Chapter 1: Plasmids and Their Usefulness in Molecular Cloning," *Molecular Cloning A Laboratory Manual*, 3rd Edition, vol. 1, Cold Spring Harbor Laboratory Press, Cold Spring, NY, 2001, p. 1.20, month not available.

Abe et al., "Destabilizing Universal Linkers for Signal Amplification in Self-Ligating Probes for RNA," *Journ. Am. Chem. Soc.*, 2004, 126:13980-13986 (WEB Pub Oct. 2004).

Du et al., "Gapped DNA and Cyclization of Short DNA Fragments," *Biophysical Journal*, 2005, 88:4137-4145 (Jun., 2005).

Hagerman, P.J. "Flexibility of DNA," *Am. Rev. Biophys. Chem.* 1988 17:265-286.

Ihara et al., "Photochemical Ligation of DNA Conjugates through Anthracene Cyclodimer Formation and its Fidelity to the Template Sequences," *Journ. Am. Chemc. Soc.*, 2004, 126:8880-8881 (WEB Published Jul. 1, 2004).

Jain et al., "Enzymatic behavior by Intercalating Molecules in a Template-Derived Ligation Reaction," *Angrew Chem. Int. Ed.* 2004, 43:2004-2008 (Apr. 2, 2004).

John et al., "Mechanics of DNA Flexibility Visulaized by Selective 2-Amine Acylation at Nucleotide Bulges," *J. Mol. Biol.* 2004, 337:611-619.

Kahn et al., "Detection of localized DNA Flexibility," *Nature*, 368:163-166 (Mar. 10, 1994).

Mills et al., "Electrophoretic Evidence that Single-Stranded Regions of One or More Nucleotides Dramatically Increase the Flexibility of DNA," *Biochemistry*, 1994, 33:1797-1803 (ACS Advanced Abstract published Feb. 1, 1994).

Oxford Dictionary of Biochemistry and Molecular Biology, Oxford University Press, New York, 1997. Definitions of "hairpin" and "bulge loop".

Roll et al., "Conformations of Nicked and Gapped DNA Structures by NMR and Molecular Dynamic Simulations in Water," *Biochemistry*, 1998, 37:4059-4070.

Sando et al., "Quenched Auto-Ligating DNAs: Multicolor Identification of Nucleic Acids at Single Nucleotide Resolution," *J. Am. Chem. Soc.,* 2004, 126:1081-1087 (WEB published on Jan. 10, 2004).

Zhang et al., "High-throughput approach for detection of DNA bending and flexibility based on cyclization," *Proc. Natl. Acad. Sci., U.S.A.* 100(6), 2003, Article retrieved from the internet (WEB published on Mar. 10, 2003). http://www.pubmedcentral.nih.gov/articlerender.fcgi?artid=152263 on Jul. 21, 2005.

* cited by examiner

3'-phosphorothioate   5'-iodothymidine   5'-bridging phos-
phorothioate linkage

3'-phosphoroselenoate   5'-iodothymidine   5'-bridging phos-
phoroselenoate linkage

| rxn.type | conversion | | isolated yield |
|---|---|---|---|
| ssDNA ligation | >90% | | 44% |
| duplex ligation | 75% | | 36% |
| ligation/cyclization | >90% | (1st step) | |
| | 50% | (2nd step) | 20% | exonuclease/hydrolysis susceptibility

5'-GATCAGGT$_{Ps}$TTCACGAGCCTG-3'  (SEQ ID NO:14)

endonuclease susceptibility

```
  T T GTACGCTGGA   TGCA Ps TCCAGCGTAC T T
  T   ||||||||||   ||||    |||||||||| T     (SEQ ID NO:16)
  T T CATGCGACCT Ps ACGT   AGGTCGCATG T T
``` template for replication / transcription

```
                              (SEQ ID NO:22)
5'-TAATACGACTCACTATA
   ||||||||||||||||
3'-ATTATGCTGAGTGATATCCTGCCTATTCCGAGCACTT Ps TGGACTAG
                              (SEQ ID NO:23)
```

*Fig. 5*

5'-bridging phosphorothioate duplex:   dumbbell (SEQ ID NO:24)   T$^T$GTACGCTGGATGCA$^S$ TCCAGCGTAC$^T$T
                 T$^T$CATGCGACCT$_S$ACGT AGGTCGCATG$_T$$^T$ all phosphodiester duplex:
                           Nsi I
(SEQ ID NO:25)   T$^T$GTACGCTGGATGCATCCAGCGTAC$^T$T
                 T$_T$CATGCGACCTACGTAGGTCGCATG$_T$$^T$ hairpin

*Fig. 7* probes (SEQ ID NO:36)

```
         3'           5'    3'       5'
         TGAGAACGGGTGT·¹ -ₚGGC[X]GCC        (X=G,T)
```

WT target
5'GTCAGCGCACTCTTGCCCACACCG[C]CGGCGCCCACCACCACCAGCTTATA3'
(SEQ ID NO:37)

MUT target
5'GTCAGCGCACTCTTGCCCACACCG[A]CGGCGCCCACCACCACCAGCTTATA3'
(SEQ ID NO:38)

| temperature (°C) | [target] (nM) | fold turnover | |
|---|---|---|---|
| | | no cycling[a] | cycling[b] |
| 22 | 1 | 24 | -- |
| | 10 | 1.6 | 1.0 |
| | 100 | 1.0 | 1.0 |
| 27 | 1 | 13 | 14 |
| | 10 | 1.6 | 3.0 |
| | 100 | 1.2 | 1.2 |
| 32 | 1 | 40 | 51 |
| | 10 | 4.6 | 4.7 |
| | 100 | 2.3 | 2.3 |
| 37 | 1 | 30 | 44 |
| | 10 | 5.9 | 6.2 |
| | 100 | 2.2 | 2.2 |

[a]Simple incubation of 10 μM probes with target for 24 hr followed by gel electrophoresis and quantitation of ligated product.
[b]24 hr of thermal cycling (30 min at temp. shown, followed by 45 sec at 95°C).

(SEQ ID NO:39)

Fig. 19
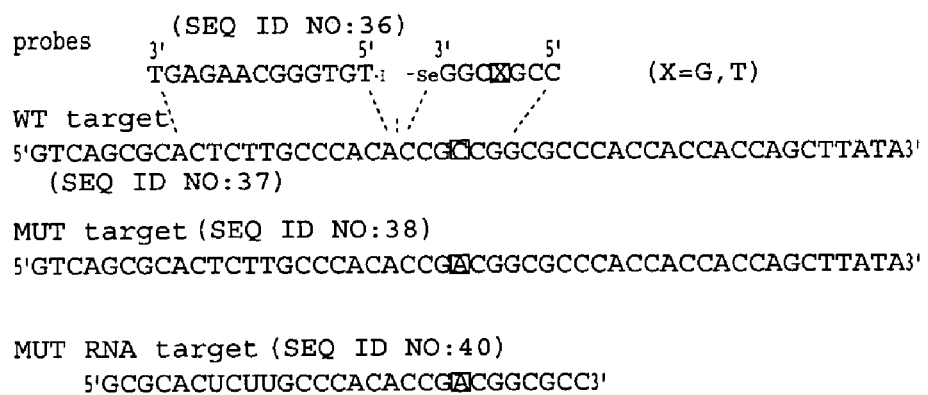
probes    (SEQ ID NO:36)
         3'         5'  3'      5'
         TGAGAACGGGTGT-¡ -seGGCXGCC       (X=G,T)
WT target
5'GTCAGCGCACTCTTGCCCACACCGCCGGCGCCCACCACCACCAGCTTATA3'
   (SEQ ID NO:37)
MUT target (SEQ ID NO:38)
5'GTCAGCGCACTCTTGCCCACACCGACGGCGCCCACCACCACCAGCTTATA3'
MUT RNA target (SEQ ID NO:40)
    5'GCGCACUCUUGCCCACACCGACGGCGCC3'
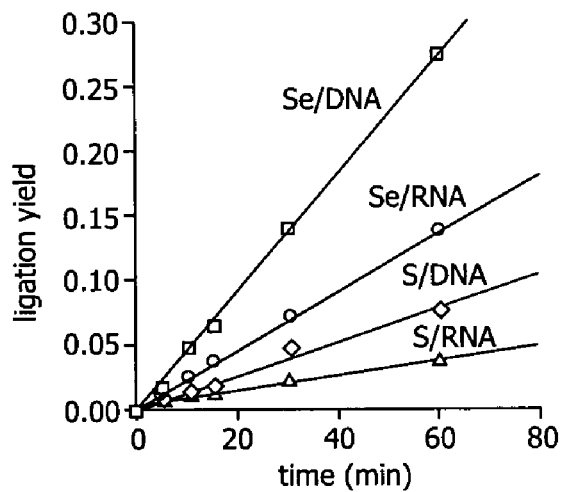
Fig. 20

SEQUENCE LISTING

```
<160> NUMBER OF SEQ ID NOS: 40

<210> SEQ ID NO 1
<211> LENGTH: 28
<212> TYPE: DNA
<213> ORGANISM: Artificial Sequence
<220> FEATURE:
<223> OTHER INFORMATION: autoligating hairpin
<221> NAME/KEY: misc_feature
<222> LOCATION: (1)..(1)
<223> OTHER INFORMATION: 5'-deoxy-5'-iodothymidine
<221> NAME/KEY: misc_feature
<222> LOCATION: (28)..(28)
```

```
<223> OTHER INFORMATION: deoxyadenosine with a phosphorothioate group on
      its 3' hydroxyl group

<400> SEQUENCE: 1
nccagcgtac ttttgtacgc tggatgcn                                    28

<210> SEQ ID NO 2
<211> LENGTH: 28
<212> TYPE: DNA
<213> ORGANISM: Artificial Sequence
<220> FEATURE:
<223> OTHER INFORMATION: hairpin

<400> SEQUENCE: 2
tccagcgtac ttttgtacgc tggatgca                                    28

<210> SEQ ID NO 3
<211> LENGTH: 12
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (1)..(1)
<223> OTHER INFORMATION: 5'-deoxy-5'-iodothymidine

<400> SEQUENCE: 3
ntcacgagcc tg                                                     12

<210> SEQ ID NO 4
<211> LENGTH: 18
<212> TYPE: DNA
<213> ORGANISM: Artificial Sequence
<220> FEATURE:
<223> OTHER INFORMATION: splint oligomer

<400> SEQUENCE: 4
ctagtccaaa gtgctcgg                                               18

<210> SEQ ID NO 5
<211> LENGTH: 20
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (1)..(1)
<223> OTHER INFORMATION: deoxyguanosine which is radiolabeled with 32P
      at its 5' end
<221> NAME/KEY: misc_feature
<222> LOCATION: (8)..(8)
<223> OTHER INFORMATION: deoxythymidine with a phosphorothioate group on
      its 3' hydroxyl group

<400> SEQUENCE: 5
natcaggntt cacgagcctg                                             20

<210> SEQ ID NO 6
<211> LENGTH: 20
<212> TYPE: DNA
<213> ORGANISM: Artificial Sequence
<220> FEATURE:
<223> OTHER INFORMATION: 20mer duplex carrying a sulfur linkage
<221> NAME/KEY: misc_feature
<222> LOCATION: (8)..(8)
<223> OTHER INFORMATION: deoxythymidine with a phosphorothioate group on
      its 3' hydroxyl group

<400> SEQUENCE: 6
```

```
gatcaggntt cacgagcctg                                              20

<210> SEQ ID NO 7
<211> LENGTH: 20
<212> TYPE: DNA
<213> ORGANISM: Artificial Sequence
<220> FEATURE:
<223> OTHER INFORMATION: sense primer

<400> SEQUENCE: 7
gtggggcagg agaccctgta                                              20

<210> SEQ ID NO 8
<211> LENGTH: 20
<212> TYPE: DNA
<213> ORGANISM: Artificial Sequence
<220> FEATURE:
<223> OTHER INFORMATION: antisense primer

<400> SEQUENCE: 8
ccctcctcta gaggaagcag                                              20

<210> SEQ ID NO 9
<211> LENGTH: 17
<212> TYPE: DNA
<213> ORGANISM: Artificial Sequence
<220> FEATURE:
<223> OTHER INFORMATION: ligated oligonucleotide

<400> SEQUENCE: 9
gtgggcgccg tcggtgt                                                 17

<210> SEQ ID NO 10
<211> LENGTH: 17
<212> TYPE: DNA
<213> ORGANISM: Artificial Sequence
<220> FEATURE:
<223> OTHER INFORMATION: ligated oligonucleotide
<221> NAME/KEY: misc_feature
<222> LOCATION: (10)..(10)
<223> OTHER INFORMATION: deoxyguanosine with a phosphorothioate group on
      its 3' hydroxyl group

<400> SEQUENCE: 10
gtgggcgccn tcggtgt                                                 17

<210> SEQ ID NO 11
<211> LENGTH: 17
<212> TYPE: DNA
<213> ORGANISM: Artificial Sequence
<220> FEATURE:
<223> OTHER INFORMATION: ligated oligonucleotide
<221> NAME/KEY: misc_feature
<222> LOCATION: (10)..(10)
<223> OTHER INFORMATION: deoxyguanosine with a phosphoroselenoate group
      on its 3' hydoxyl group

<400> SEQUENCE: 11
gtgggcgccn tcggtgt                                                 17

<210> SEQ ID NO 12
<211> LENGTH: 12
<212> TYPE: DNA
<213> ORGANISM: Artificial Sequence
<220> FEATURE:
<223> OTHER INFORMATION: ssDNA starting sequence
<221> NAME/KEY: misc_feature
```

```
<222> LOCATION: (1)..(1)
<223> OTHER INFORMATION: 5'-deoxy-5'-iodothymidine

<400> SEQUENCE: 12
ntcacgagcc tg                                                          12

<210> SEQ ID NO 13
<211> LENGTH: 18
<212> TYPE: DNA
<213> ORGANISM: Artificial Sequence
<220> FEATURE:
<223> OTHER INFORMATION: ssDNA template

<400> SEQUENCE: 13
ggctcgtgaa acctgatc                                                    18

<210> SEQ ID NO 14
<211> LENGTH: 20
<212> TYPE: DNA
<213> ORGANISM: Artificial Sequence
<220> FEATURE:
<223> OTHER INFORMATION: product of ssDNA ligation
<221> NAME/KEY: misc_feature
<222> LOCATION: (8)..(8)
<223> OTHER INFORMATION: deoxythymidine with a phosphorothioate group on
      its 3' hydroxyl group

<400> SEQUENCE: 14
gatcaggntt cacgagcctg                                                  20

<210> SEQ ID NO 15
<211> LENGTH: 28
<212> TYPE: DNA
<213> ORGANISM: Artificial Sequence
<220> FEATURE:
<223> OTHER INFORMATION: duplex DNA starting sequence
<221> NAME/KEY: misc_feature
<222> LOCATION: (1)..(1)
<223> OTHER INFORMATION: 5'-deoxy-5'-iodothymidine
<221> NAME/KEY: misc_feature
<222> LOCATION: (28)..(28)
<223> OTHER INFORMATION: deoxyadenosine with a phosphorothioate group on
      its 3' hydroxyl group

<400> SEQUENCE: 15
nccagcgtac ttttgtacgc tggatgcn                                         28

<210> SEQ ID NO 16
<211> LENGTH: 56
<212> TYPE: DNA
<213> ORGANISM: Artificial Sequence
<220> FEATURE:
<223> OTHER INFORMATION: circular product of duplex DNA ligation
<221> NAME/KEY: misc_feature
<222> LOCATION: (1)..(1)
<223> OTHER INFORMATION: deoxythymidine with a 5'-bridging
      phosphothioester linking group where sulfur is in the 5'-bridging
      position
<221> NAME/KEY: misc_feature
<222> LOCATION: (29)..(29)
<223> OTHER INFORMATION: deoxythymidine with a 5'-bridging
      phosphothioester linking group where sulfur is in the 5'-bridging
      position

<400> SEQUENCE: 16
nccagcgtac ttttgtacgc tggatgcanc cagcgtactt tgtacgctg gatgca           56

<210> SEQ ID NO 17
<211> LENGTH: 20
```

```
<212> TYPE: DNA
<213> ORGANISM: Artificial Sequence
<220> FEATURE:
<223> OTHER INFORMATION: splint oligomer

<400> SEQUENCE: 17
acggtccaaa acatattttg                                           20

<210> SEQ ID NO 18
<211> LENGTH: 30
<212> TYPE: DNA
<213> ORGANISM: Artificial Sequence
<220> FEATURE:
<223> OTHER INFORMATION: one-pot ligation oligonucleotide
<221> NAME/KEY: misc_feature
<222> LOCATION: (1)..(1)
<223> OTHER INFORMATION: 5'-deoxy-5'-iodothymidine
<221> NAME/KEY: misc_feature
<222> LOCATION: (30)..(30)
<223> OTHER INFORMATION: deoxythymidine with a phosphorothioate group on
      its 3' hydroxyl group

<400> SEQUENCE: 18
ngatcacttc gtctcttcag caaaatatgn                                30

<210> SEQ ID NO 19
<211> LENGTH: 33
<212> TYPE: DNA
<213> ORGANISM: Artificial Sequence
<220> FEATURE:
<223> OTHER INFORMATION: one-pot ligation oligonucleotide
<221> NAME/KEY: misc_feature
<222> LOCATION: (1)..(1)
<223> OTHER INFORMATION: 5'-deoxy-5'-iodothymidine
<221> NAME/KEY: misc_feature
<222> LOCATION: (33)..(33)
<223> OTHER INFORMATION: deoxythymidine with a phosphorothioate group on
      its 3' hydroxyl group

<400> SEQUENCE: 19
nttggaccgt tggtttcgac ttgtcagagg acn                            33

<210> SEQ ID NO 20
<211> LENGTH: 18
<212> TYPE: DNA
<213> ORGANISM: Artificial Sequence
<220> FEATURE:
<223> OTHER INFORMATION: splint oligonucleotide

<400> SEQUENCE: 20
agtgatcaag tcctctga                                             18

<210> SEQ ID NO 21
<211> LENGTH: 63
<212> TYPE: DNA
<213> ORGANISM: Artificial Sequence
<220> FEATURE:
<223> OTHER INFORMATION: circular product of one-pot ligation
<221> NAME/KEY: misc_feature
<222> LOCATION: (1)..(1)
<223> OTHER INFORMATION: deoxythymidine with a 5'-bridging
      phosphothioester linking group where sulfur is in the 5'-bridging
      position
<221> NAME/KEY: misc_feature
<222> LOCATION: (34)..(34)
<223> OTHER INFORMATION: deoxythymidine with a 5'-bridging
      phosphothioester linking group where sulfur is in the 5'-bridging
      position

<400> SEQUENCE: 21
```

```
nttggaccgt tggtttcgac ttgtcagagg actngatcac ttcgtctctt cagcaaaata    60
tgt                                                                  63

<210> SEQ ID NO 22
<211> LENGTH: 17
<212> TYPE: DNA
<213> ORGANISM: Artificial Sequence
<220> FEATURE:
<223> OTHER INFORMATION: 18mer complementary strand

<400> SEQUENCE: 22
taatacgact cactata                                                   17

<210> SEQ ID NO 23
<211> LENGTH: 45
<212> TYPE: DNA
<213> ORGANISM: Artificial Sequence
<220> FEATURE:
<223> OTHER INFORMATION: template for replication/transcription
<221> NAME/KEY: misc_feature
<222> LOCATION: (9)..(9)
<223> OTHER INFORMATION: deoxythymidine with a 5'-bridging
      phosphothioester linking group where sulfur is in the 5'-bridging
      position

<400> SEQUENCE: 23
gatcaggtnt cacgagcctt atccgtccta tagtgagtcg tatta                    45

<210> SEQ ID NO 24
<211> LENGTH: 58
<212> TYPE: DNA
<213> ORGANISM: Artificial Sequence
<220> FEATURE:
<223> OTHER INFORMATION: 5'-bridging phosphorothioate duplex DNA
<221> NAME/KEY: misc_feature
<222> LOCATION: (1)..(1)
<223> OTHER INFORMATION: deoxythymidine with a 5'-bridging
      phosphorothioate linking group where sulfur is in the 5'-bridging
      position
<221> NAME/KEY: misc_feature
<222> LOCATION: (31)..(31)
<223> OTHER INFORMATION: deoxythymidine with a 5'-bridging
      phosphorothioate linking group where sulfur is in the 5'-bridging
      position

<400> SEQUENCE: 24
nccagcgtat cttttgatac gctggatgca nccagcgtac ttttgtacgc tggatgca      58

<210> SEQ ID NO 25
<211> LENGTH: 58
<212> TYPE: DNA
<213> ORGANISM: Artificial Sequence
<220> FEATURE:
<223> OTHER INFORMATION: all phosphodiester DNA

<400> SEQUENCE: 25
tccagcgtat cttttgatac gctggatgca tccagcgtac ttttgtacgc tggatgca      58

<210> SEQ ID NO 26
<211> LENGTH: 10
<212> TYPE: DNA
<213> ORGANISM: Artificial Sequence
<220> FEATURE:
<223> OTHER INFORMATION: linear autoligation probe
<221> NAME/KEY: misc_feature
<222> LOCATION: (10)..(10)
<223> OTHER INFORMATION: deoxyguanosine with a phosphorothioate group on
      its 3' hydroxyl group
```

-continued

```
<400> SEQUENCE: 26 gtgggcgccn                                                          10

<210> SEQ ID NO 27
<211> LENGTH: 28
<212> TYPE: DNA
<213> ORGANISM: Artificial Sequence
<220> FEATURE:
<223> OTHER INFORMATION: MUT target

<400> SEQUENCE: 27
cttacccaca ccgacggagc ccaccacc                                      28

<210> SEQ ID NO 28
<211> LENGTH: 28
<212> TYPE: DNA
<213> ORGANISM: Artificial Sequence
<220> FEATURE:
<223> OTHER INFORMATION: 5'MM target

<400> SEQUENCE: 28
cttacccaca ccgccggagc ccaccacc                                      28

<210> SEQ ID NO 29
<211> LENGTH: 28
<212> TYPE: DNA
<213> ORGANISM: Artificial Sequence
<220> FEATURE:
<223> OTHER INFORMATION: 3'MM target

<400> SEQUENCE: 29
cttacccaca ccgaaggagc ccaccacc                                      28

<210> SEQ ID NO 30
<211> LENGTH: 28
<212> TYPE: DNA
<213> ORGANISM: Artificial Sequence
<220> FEATURE:
<223> OTHER INFORMATION: MMM target

<400> SEQUENCE: 30
cttacccaca cggacggagc ccaccacc                                      28

<210> SEQ ID NO 31
<211> LENGTH: 48
<212> TYPE: DNA
<213> ORGANISM: Artificial Sequence
<220> FEATURE:
<223> OTHER INFORMATION: cyclization probe
<221> NAME/KEY: misc_feature
<222> LOCATION: (1)..(1)
<223> OTHER INFORMATION: 5'-deoxy-5'-iodothymidine
<221> NAME/KEY: misc_feature
<222> LOCATION: (48)..(48)
<223> OTHER INFORMATION: deoxyguanosine with a phosphorothioate group on
      its 3' hydroxyl group

<400> SEQUENCE: 31
ncggtgtggg ttttcactga atatcacgat tacattttgt gggcgccn                48

<210> SEQ ID NO 32
<211> LENGTH: 28
<212> TYPE: DNA
<213> ORGANISM: Artificial Sequence
<220> FEATURE:
<223> OTHER INFORMATION: MMM target
```

```
<400> SEQUENCE: 32
cttacccaaa ccgacggagc ccaccacc                                          28

<210> SEQ ID NO 33
<211> LENGTH: 28
<212> TYPE: DNA
<213> ORGANISM: Artificial Sequence
<220> FEATURE:
<223> OTHER INFORMATION: MUT target

<400> SEQUENCE: 33
cttgaaaacc cacaccgacg gcgcatca                                          28

<210> SEQ ID NO 34
<211> LENGTH: 28
<212> TYPE: DNA
<213> ORGANISM: Artificial Sequence
<220> FEATURE:
<223> OTHER INFORMATION: 3'MM target

<400> SEQUENCE: 34
cttgaaaacc cacaccgaag gcgcatca                                          28

<210> SEQ ID NO 35
<211> LENGTH: 28
<212> TYPE: DNA
<213> ORGANISM: Artificial Sequence
<220> FEATURE:
<223> OTHER INFORMATION: MMM target

<400> SEQUENCE: 35
cttgaaaacc cacaccgacg tcgcatca                                          28

<210> SEQ ID NO 36
<211> LENGTH: 13
<212> TYPE: DNA
<213> ORGANISM: Artificial Sequence
<220> FEATURE:
<223> OTHER INFORMATION: linear probe
<221> NAME/KEY: misc_feature
<222> LOCATION: (1)..(1)
<223> OTHER INFORMATION: 5'-deoxy-5'-iodothymidine

<400> SEQUENCE: 36
ngtgggcaag agt                                                          13

<210> SEQ ID NO 37
<211> LENGTH: 50
<212> TYPE: DNA
<213> ORGANISM: Artificial Sequence
<220> FEATURE:
<223> OTHER INFORMATION: wild-type target

<400> SEQUENCE: 37
gtcagcgcac tcttgcccac accgccggcg cccaccacca ccagcttata                  50

<210> SEQ ID NO 38
<211> LENGTH: 50
<212> TYPE: DNA
<213> ORGANISM: Artificial Sequence
<220> FEATURE:
<223> OTHER INFORMATION: mutant H-ras target

<400> SEQUENCE: 38
gtcagcgcac tcttgcccac accgacggcg cccaccacca ccagcttata                  50
```

```
<210> SEQ ID NO 39
<211> LENGTH: 13
<212> TYPE: DNA
<213> ORGANISM: Artificial Sequence
<220> FEATURE:
<223> OTHER INFORMATION: universal probe
<221> NAME/KEY: misc_feature
<222> LOCATION: (1)..(1)
<223> OTHER INFORMATION: 5'deoxy-5'-iodothymidine
<221> NAME/KEY: misc_feature
<222> LOCATION: (3)..(3)
<223> OTHER INFORMATION: fluorescein-dT

<400> SEQUENCE: 39
ngngggcaag agt                                                      13

<210> SEQ ID NO 40
<211> LENGTH: 28
<212> TYPE: RNA
<213> ORGANISM: Artificial Sequence
<220> FEATURE:
<223> OTHER INFORMATION: H-ras oncogene target

<400> SEQUENCE: 40
gcgcacucuu gcccacaccg acggcgcc                                      28
```

COMPOSITIONS AND METHODS FOR NONENZYMATIC LIGATION OF OLIGONUCLEOTIDES AND DETECTION OF GENETIC POLYMORPHISMS

This application claims the benefit of U.S. Provisional Application Ser. No. 60/116,059, filed 15 Jan. 1999.

STATEMENT OF GOVERNMENT RIGHTS

This invention was made with government support under a grant from the National Institutes of Health, Grant No. R01-GM46625. The U.S. Government has certain rights in this invention.

BACKGROUND OF THE INVENTION

Once the genome is sequenced, the second phase of the Humane Genome Project is aimed at surveying single nucleotide polymorphisms (SNPs) that exist in different human DNAs. It is now clear that changes in sequence as small as a single base in a gene can be diagnostic for many disease states and susceptibilities. As a result, in the future the medical community will commonly make use of genetic screens of individual patients as a routine part of diagnosis. This means that the development of rapid, sensitive, and accurate methods for detecting and identifying SNPs is very important to the future of medicine.

One type of SNP that has been recognized as very important to diagnosis of cancer is the set of single-base mutations that have been associated with the development of cancer. An increasing number of point mutations in oncogenes and tumor suppressor genes have been linked to cancer, and some of these are not merely diagnostic (i.e., associated with cancer) but also causative (responsible for the cancerous phenotype). Among the most important examples already starting to be screened in medical laboratories today are point mutations in the H-ras and K-ras oncogene family as well as in the p53 tumor suppressor gene. In some kinds of cancer, such point mutations are strongly specific; for example, a single K-ras codon 12 point mutation is found in ~90% of all pancreatic cancers.

SNPs can be detected using various DNA ligation strategies. Methods for joining strands of DNA are widely used in chemistry, molecular biology, and biomedicine. Both enzymatic and chemical methods for DNA ligation are known. Enzymatic ligation of DNA has been important for the development of DNA diagnostic methods. Moreover, current methods for enzymatic DNA ligation cannot be used for direct detection of RNAs, since these ligases require duplex DNAs as substrates. In addition, although very short probes exhibit the highest sequence specificity, ligase enzymes cannot utilize oligodeoxynucleotides shorter than about 9 nucleotides (C. Pritchard et al., Nucleic Acids Res. 25: 3403–3407 (1997)). Also, because of the sensitivity to native DNA structure, ligase-mediated approaches are unlikely to be useful with modified probes that contain nonnatural DNA structure such as PNA, phosphoramidate DNA, or 2'-O-methyl RNA. Even relatively simple modifications such as conjugation with biotin or fluorescent labels may be expected to cause difficulties near the ligation junction. Finally, ligase methods are not likely to be useful in intact cellular or tissue preparations, since it would be difficult to deliver the ligase into cells.

By comparison, nonenzymatic ligation strategies have the advantage of not requiring natural structure at the ligation site and, potentially, of proceeding in higher yields at lower cost. Some nonenzymatic ligation approaches require reducing reagents such as borohydride, oxidizing reagents such as ferricyanide, condensing reagents such as carbodiimides or cyanoimidazole, or UV irradiation to carry out the reaction. Other nonenzymatic ligations, termed autoligations or self-ligations, proceed in the absence of additional reagents. While the need for added reagents is not limiting in many situations, autoligation is simpler, and might be carried out in media where reagents are inactive or where they will affect biochemical processes.

Letsinger et al. (U.S. Pat. No. 5,476,930) have described an irreversible, nonenzymatic, covalent autoligation of adjacent, template-bound oligodeoxynucleotides wherein one oligonucleotide has a 5' or 3' α-haloacyl reactive group, such as a 3'-bromoacetylamino, and the second oligonucleotide has a 3' or 5' phosphorothioate group. The resulting linkage takes the form of a thiophosphorylacetylamino bond.

Letsinger et al. (U.S. Pat. No. 5,780,613; Herrlein et al., J. Am. Chem. Soc., 117, 10151 (1995)) have also described an approach to the templated ligation of oligodeoxynucleotides that involves reacting an oligonucleotide having a 3'-phosphorothioate group with a second oligonucleotide having as 5' tosylate leaving group giving $S_N2$ displacement and resulting in more natural DNA structure, having a sulfur atom replacing one of the bridging phosphodiester oxygen atoms. This method was used to ligate self-templated ends to yield dumbbell-type structures in good yields. However, due to the reactivity of the 5'-tosylate to ammonia, it was necessary to use labile protecting groups and rapid deprotection, and significant degradation was still observed for oligonucleotides carrying the reactive leaving group. Xu et al. (Tetrahedron Lett., 38, 5595–5598 (1997)) describe an improvement in this method utilizing, as the leaving group, a 5'-iodide which is stable to ammonia deprotection.

There is a clear need for simple, rapid and reliable methods for detecting SNPs, and there will be many formats in which they will be applied, such as in sequence detection in PCR-amplified DNAs, detection in DNAs or in RNAs isolated directly from clinical samples (blood, tissue, urine, etc), detection in isolated cells (such as from blood), detection in tissue cross sections (such as from biopsies), and detection in the living body. Because of the advantages of nonenzymatic ligation methods in both diagnostic and preparative nucleic acid technologies, further improvements in the speed, selectivity and specificity of nonenzymatic ligation of oligonucleotides are very important. An improved ligation chemistry (1) would require no added reagents to carry out the reaction, (2) would require no post-synthesis modification of the DNA prior to reaction, (3) could be carried out on an RNA template (unlike enzymatic ligations), and (4) would create a junction that causes little perturbation to the DNA structure.

SUMMARY OF THE INVENTION

The invention is directed to novel compositions and methods for nonenzymatic ligation of oligonucleotides.

In one aspect, the invention is directed to a nucleotide containing a phosphoroselenoate group or a phosphorotelluroate group, as well as an oligonucleotide having such nucleotide at its 3' end. The invention is further directed to a 5' iodonucleoside including 5'-deoxy-5'-iodothymidine (5'-I-T), 5'-deoxy-5'-iodo-2'-deoxycytidine (5'-I-dC), 5'-deoxy-5'-iodo-2'-deoxyadenosine (5'-I-dA), 5'-deoxy-5'-iodo-3-deaza-2'-deoxyadenosine (5'-I-3-deaza-dA), 5'-deoxy-5'-iodo-2'-deoxyguanosine (5'-I-dG), 5'-deoxy-5'-iodo-3-deaza-2'-deoxyguanosine (5'-I-3-deaza-dG), 5'-deoxy-5'-iodouracil (5'-I-U), 5'-deoxy-5'-iodocytidine (5'-I-C), 5'-deoxy-5'-iodoadenosine (5'-I-A), 5'-deoxy-5'-iodo-3-deazaadenosine (5'-I-3-deaza-A), 5'-deoxy-5'-iodoguanosine (5'-I-G) and 5'-deoxy-5'-iodo-3-deazaguanosine (5'-I-3-deaza-G), and the phosphoroamidite derivatives thereof, as well as the related nucleotides and an oligonucleotide having at its 5' end such a 5'-deoxy-5'-iodonucleotide. Methods of making the 5'-deoxy-5'-iodonucleosides of the invention are also included.

Also included in the invention is an oligonucleotide that has, at its 3' end, a phosphoroselenoate group or a phosphorotelluroate group and, at its 5' end, a nucleoside comprising a 5' leaving group.

The invention further includes an oligonucleotide formed from two or more 2'-deoxyribonucleotides and one ribonucleotide. In one embodiment, the ribonucleotide is positioned at the 3' end of the oligonucleotide and contains a phosphorothioate group, a phosphoroselenoate group or a phosphorotelluroate group. In another embodiment, the ribonucleotide is positioned at the 5' end of the oligonucleotide and contains a 5' leaving group.

In another aspect, the invention provides a solid support having attached to it one or more oligonucleotides as described herein, including but not limited to an oligonucleotide containing a phosphorothioate group, a phosphoroselenoate group, or a phosphorotelluroate group; an oligonucleotide comprising a 5' leaving group, including an oligonucleotide containing an α-haloacyl group; an oligonucleotide containing one or more deoxyribonucleotides; and an oligonucleotide containing one or more ribonucleotides.

In yet another aspect, the invention provides an oligonucleotide containing at least one 5' bridging phosphoroselenoester or phosphorotelluroester. The oligonucleotide can be a DNA or an RNA oligonucleotide, or can contain a combination of one or more deoxyribonucleotides and one or more ribonucleotides. It can be circular or linear. In a preferred embodiment, the bridging phosphoroselenoester or phosphorotelluroester forms a bridge between a deoxyribonucleotide and a ribonucleotide. Also included is a nucleic acid duplex formed from the hybridization of the selenium-containing or tellurium-containing oligonucleotide hybridized to a complementary oligonucleotide.

In another aspect, the invention is directed to a method for making an oligonucleotide that includes binding at least one upstream oligonucleotide and at least one downstream oligonucleotide to a polynucleotide template to yield an autoligated oligonucleotide product formed from the upstream oligonucleotide ligated to the downstream oligonucleotide. The polynucleotide template can be DNA or RNA, and can be double-stranded or single-stranded. Multiple oligonucleotides can be used, in which event the middle oligonucleotides serve as both upstream and downstream oligonucleotides. The upstream oligonucleotide includes, as its 5' end, a nucleoside having a 5' leaving group, and the downstream oligonucleotide includes, as its 3' end, a nucleoside containing a 3' phosphoroselenoate or a 3' phosphorotelluroate. The downstream oligonucleotide binds such that its 3' end is substantially adjacent to the 5' end of the upstream oligonucleotide. In embodiments of the method in which the end of the upstream oligonucleotide is substantially but not directly adjacent to an end of the downstream oligonucleotide; in which the polynucleotide template is RNA; or in which one or more oligonucleotide of less than 7 nucleotides in length are used; the downstream oligonucleotide can contain, instead of the 3' phosphoroselenoate and a 3' phosphorotelluroate, a 3' phosphorothioate group. In a preferred embodiment, one of the oligonucleotides contains a fluorescence energy donor group and the other contains a fluorescence energy acceptor group. The presence or absence of the autoligated oligonucleotide product is accompanied by a detectable change in fluorescence emission of the ligated product compared to the fluorescence energy emissions of the unligated oligonucleotides.

In yet another aspect, the invention provides a method for detecting a genetic polymorphism in a target polynucleotide. The target polynucleotide can be DNA or RNA, and can be double-stranded or single-stranded. A target polynucleotide containing a genetic polymorphism is contacted with a universal oligonucleotide probe and a mutant polymorphism oligonucleotide probe to yield an autoligated oligonucleotide product comprising the universal oligonucleotide probe and the mutant polymorphism probe. The mutant polymorphism oligonucleotide probe is complementary to a region on the target polynucleotide that comprises the genetic polymorphism, and the universal oligonucleotide probe is capable of binding to the target polynucleotide at a region that is conserved in the analogous wild-type polynucleotide. Preferably, the nucleotide position of the suspected genetic polymorphism on the polynucleotide target does not correspond to the nucleotide position of the ligation junction end of the mutant polymorphism probe. Rather, it is preferred that the site or sites on the mutant polymorphism probe that correspond to the genetic polymorphism on the target polynucleotide be positioned toward the middle of the probe. The mutant polymorphism probe is preferably about 3 to about 12 nucleotides in length; in some applications, it is preferably about 3 to about 6 nucleotides in length. One of the oligonucleotide probes constitutes an upstream oligonucleotide that contains, as its 5' end, a nucleoside comprising a 5' leaving group, while the other oligonucleotide probe constitutes a downstream oligonucleotide that contains, as its 3' end, a nucleoside containing a 3' phosphoroselenoate or a 3' phosphorotelluroate. When both probes are bound to the target polynucleotide, an end of the universal oligonucleotide probe is substantially adjacent to an end of the mutant polymorphism oligonucleotide probe so as to position the 5' leaving group and the 3' phosphoroselenoate or 3' phosphorotelluroate in close proximity to one another. Detection of an autoligated oligonucleotide product indicates that the polynucleotide target contained the genetic polymorphism. To facilitate detection, either the mutant polymorphism oligonucleotide probe or the universal oligonucleotide probe, or both, can include a detectable label. Alternatively or in addition, one oligonucleotide probe can include a fluorescence energy donor group while the other includes a fluorescence energy acceptor group. In that event, the presence or absence of the autoligated oligonucleotide product is accompanied by a detectable change in fluorescence emission of the ligated product compared to the fluorescence emissions of the unligated oligonucleotides. In embodiments of the method in which the end of the bound universal oligonucleotide probe is substantially but not directly adjacent to an end of the bound mutant polymorphism oligonucleotide probe; in which the polynucleotide target is RNA; or in which mutant probes of less than 7 nucleotides in length are used; the downstream oligonucleotide can contain, instead of the 3' phosphoroselenoate and a 3' phosphorotelluroate, a 3' phosphorothioate group.

In yet another aspect, the invention is directed to a general method for detecting a genetic polymorphism in a target polynucleotide using fluorescence energy resonance transfer (FRET).

A target polynucleotide, as described above, is contacted with a universal oligonucleotide probe and at least one mutant polymorphism oligonucleotide probe to yield an autoligated oligonucleotide product comprising the universal oligonucleotide probe and a mutant polymorphism probe. When two oligonucleotide probes are used, one constitutes an upstream oligonucleotide having, as its 5' end, a nucleoside comprising a 5' leaving group and the other constitutes a downstream oligonucleotide containing, as its 3' end, a nucleoside comprising a functional group selected from the group consisting of a 3' phosphorothioate, a 3' phosphoroselenoate and a 3' phosphorotelluroate. When both probes are bound to the target polynucleotide, an end of the universal oligonucleotide probe is substantially adjacent to an end of the mutant polymorphism oligonucleotide probe so as to position the 5' leaving group and the 3' phosphoroselenoate or the 3' phosphorotelluroate in close proximity to one another. Additionally, one of the oligonucleotide probes contains a fluorescence energy donor group and the other oligonucleotide contains a fluorescence energy acceptor group. The presence or absence of an autoligated oligonucleotide product is accompanied by a detectable change in fluorescence emission of the ligated product compared to the fluorescence emissions of the unligated oligonucleotides, which is detected using FRET.

The invention is further directed to a method for using 3-color FRET to determine whether a target polynucleotide contains a genetic polymorphism. A target polynucleotide, as described above, is contacted with the universal oligonucleotide probe, a mutant polymorphism oligonucleotide probe and a wild-type polymorphism oligonucleotide probe to yield an autoligated oligonucleotide product that includes the universal oligonucleotide probe either the mutant polymorphism probe or the wild-type polymorphism oligonucleotide probe. The wild-type polymorphism oligonucleotide probe is complementary to a region on the analogous wild-type polynucleotide that is analogous to the region comprising the genetic polymorphism. The universal probe contains a fluorescence energy donor group; the mutant polymorphism probe contains a first fluorescence energy acceptor group; and wild-type polymorphism oligonucleotide probe includes a second energy acceptor group. Either (i) the universal oligonucleotide probe constitutes an upstream oligonucleotide comprising, as its 5' end, a nucleoside having a 5' leaving group and both polymorphism oligonucleotide probes constitute downstream oligonucleotides comprising, as their 3' ends, a nucleoside containing a 3' functional group selected from the group consisting of a 3' phosphorothioate, a 3' phosphoroselenoate and a 3' phosphorotelluroate; or (ii) both polymorphism oligonucleotide probes constitute upstream oligonucleotides having, as their 5' ends, a nucleoside comprising a 5' leaving group and the universal oligonucleotide probe constitutes a downstream oligonucleotide comprising, as its 3' end, a nucleoside containing a 3' functional group selected from the group consisting of a 3' phosphorothioate, a 3' phosphoroselenoate and a 3' phosphorotelluroate. When a universal probe and a polymorphism probe are bound to the target polynucleotide, an end of the universal oligonucleotide probe is substantially adjacent to an end of the polymorphism oligonucleotide probe so as to position the 5' leaving group and the 3' functional group in close proximity to one another. The autoligated oligonucleotide product is excited so as to cause fluorescence, and the fluorescence emission is analyzed to determine whether the autoligated oligonucleotide product comprises the mutant polymorphism probe or the wild-type polymorphism oligonucleotide probe. The presence of the mutant polymorphism probe in the autoligated oligonucleotide product indicates the presence of a genetic polymorphism in the target polynucleotide.

Methods of making oligonucleotides or detecting genetic polymorphisms that make use of FRET to detect the presence or absence of an autoligation product can, without limitation, instead utilize pyrenes at the 5' and 3' reactive ends of the upstream and downstream oligonucleotides, respectively, such the presence or absence of the autoligated oligonucleotide product is detectable using pyrene excimers as labels.

BRIEF DESCRIPTION OF THE DRAWINGS

FIG. 5 shows sequences of autoligation precursor DNAs and products obtained after ligation, where "$p_s$" denotes 5'-bridging phosphorothioester linkage.

FIG. 7 shows attempted cleavage of a short duplex DNA containing 5' bridging phosphorothioate linkages by the restriction endonuclease Nsi I; the sulfur linkage (denoted by "s") occurs in both strands between the two nucleotides where cleavage is performed by the enzyme; for comparison the cleavage of the same duplex lacking the sulfur linkages is shown.

Figure 8:
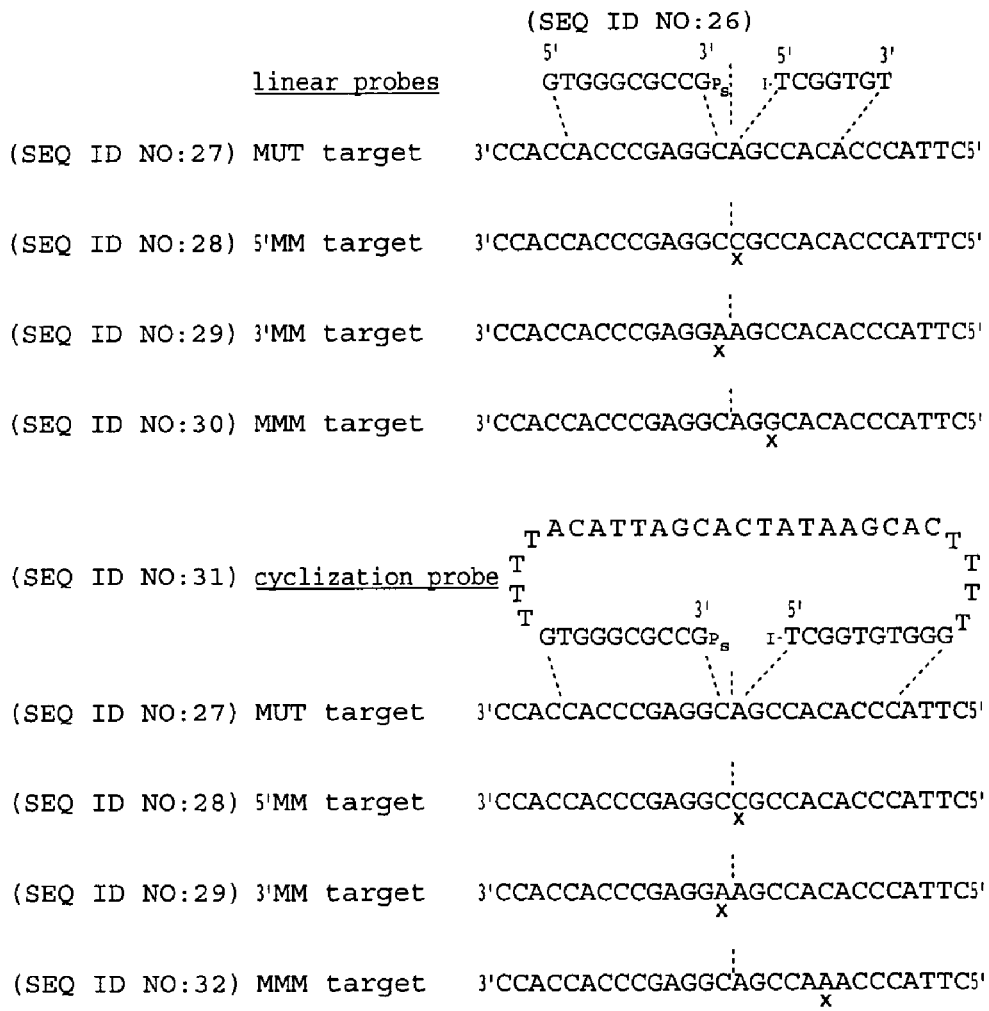

FIG. 8 shows sequences of autoligation probes and DNA targets; mismatches between probes and targets are denoted by "x"; target sequences are derived from H-ras; the 3'MM target corresponds to the protooncogene sequence and MUT, the codon 12 oncogenic mutation; the 3' end phosphorothioate groups are denoted by "$p_s$", and iodothymidine by "I-T".

Figure 9A:
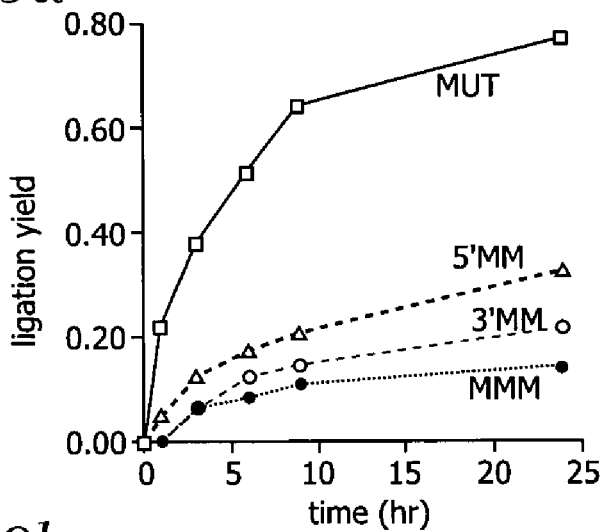
Figure 9B:
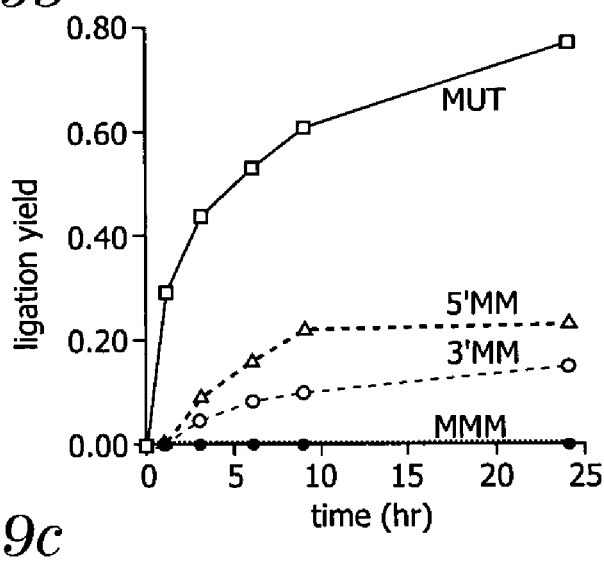
Figure 9C:
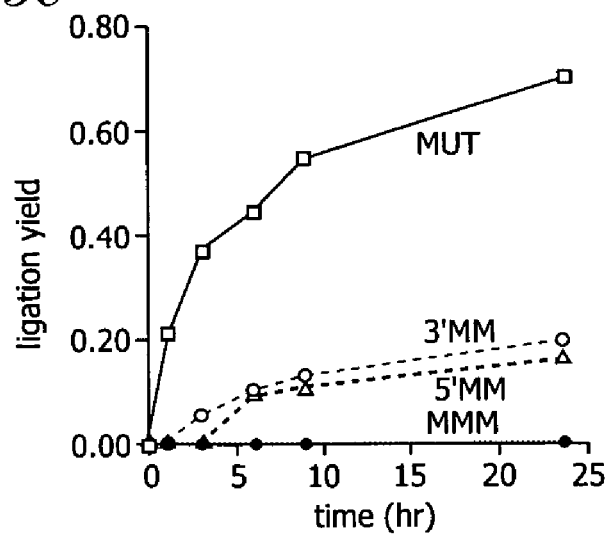

FIG. 9 shows the effects of varied conditions on autoligation yields for 7mer+10mer probes; (a) time course of ligation at 25° C. with 20 µM probe concentration; (b) time course of ligation at 25° C. with 1.3 µM probe concentration; (c) time course at 37° C. with 1.3 µM probe concentration.

Figure 10A:
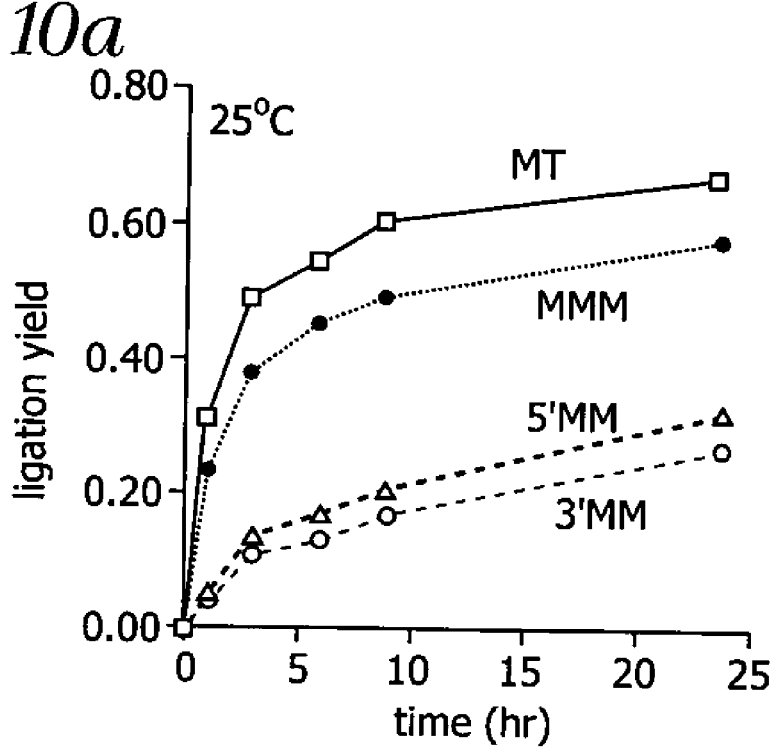
Figure 10B:
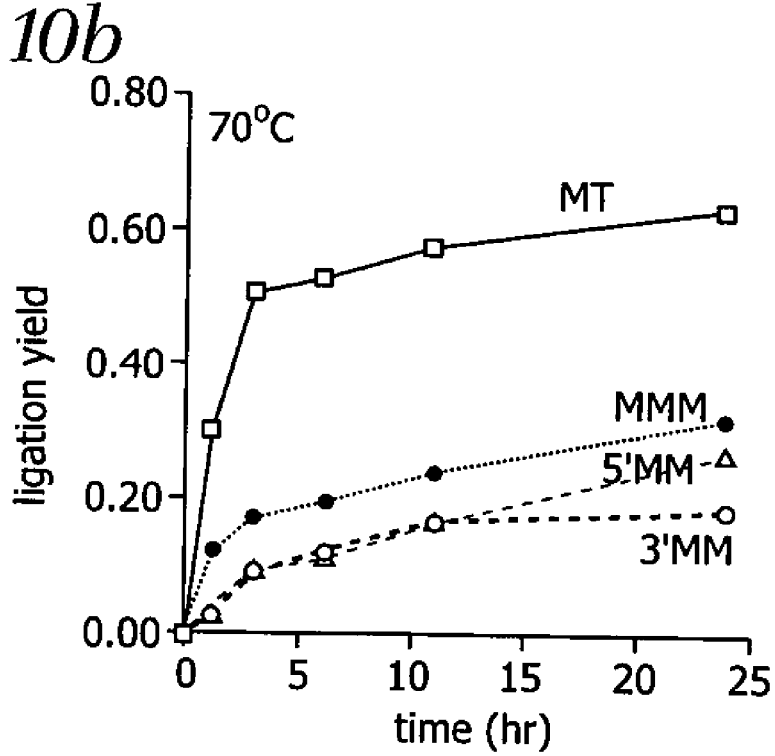

FIG. 10 shows the effects of varied conditions on autoligation yields for 48mer cyclization probe having 10 nt of possible complementarity on either side of the junction; (a)

time course of ligation at 25° C. with 1.3 μM probe concentration; (b) time course at 70° C. with 1.3 μM probe concentration.

FIG. 11 shows the effects of ligation junction placement on autoligation yields for 48mer cyclization probe having 6 and 14 nt of possible complementarity on the two sides of the junctions; (a) sequences of probe and target DNAs (b) time course of ligation at 70° C. with 1.3 μM probe concentration.

Figure 12A:
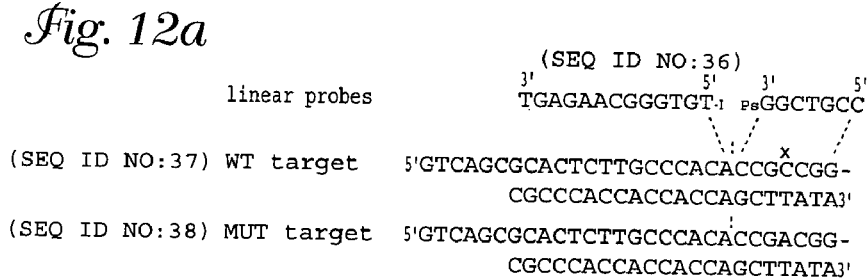
Figure 12B:
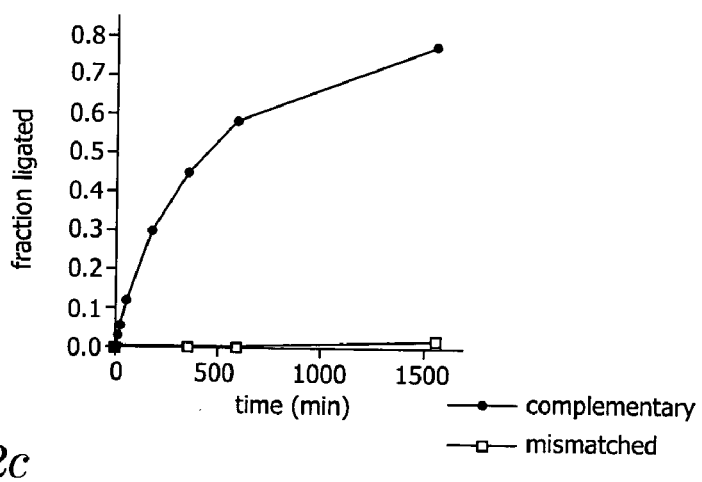
Figure 12C:
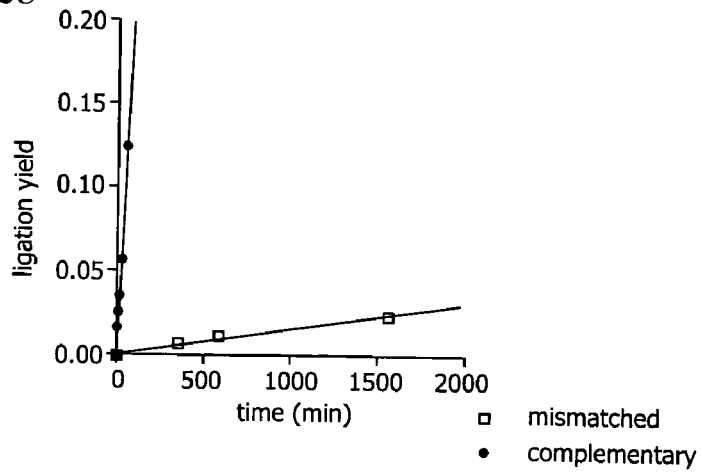

FIG. 12 shows optimized ligation of 7 and 13 nt probes on wild-type and codon 12 mutant H-ras DNA 50mer target strands, showing selectivity of probes for codon 12 mutant target; ligation is monitored by use of a radiolabeled 7mer probe; (a) sequences of H-ras optimized probes; (b) time course of ligation at 37° C. with 1.3 μM probe concentration; (c) early time course showing initial-rate linear fits; correlation coefficients are 0.999 or better.

Figure 13:

FIG. 13 depicts the probe and target sequences utilized in Example IV; iodine end groups are marked with "5'-I", and 3' end phosphorothioate groups by "S".

Figure 14A:
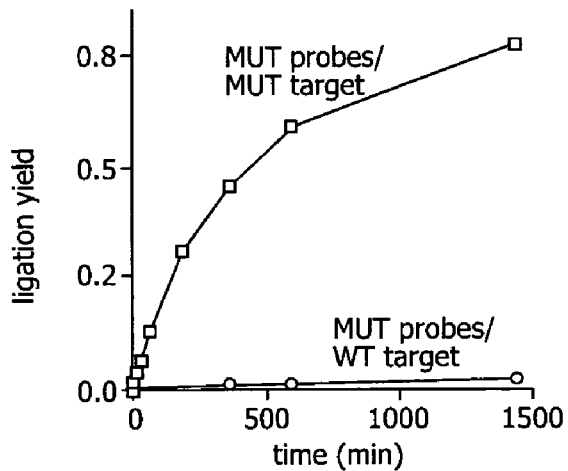
Figure 14B:
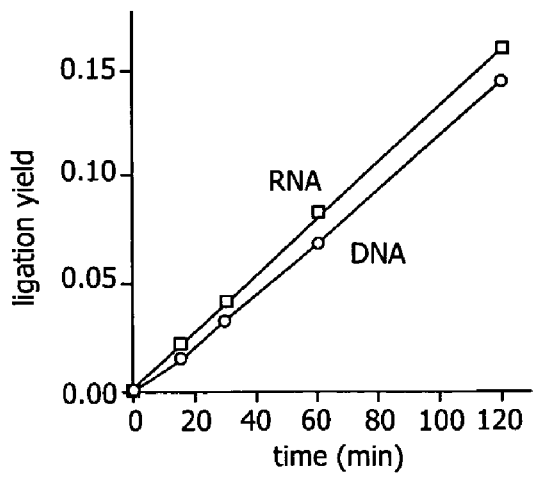

FIG. 14 depicts time courses of autoligation (a) differing rates of autoligation on matched and singly-mismatched target DNA strands; (b) relative autoligation rates on DNA and RNA target strands of identical sequence.

FIG. 15 depicts (a) turnover data for autoligation and (b) a graph showing excess ligated products generated per equivalent of target DNA.

Figure 16A:
Figure 16B:
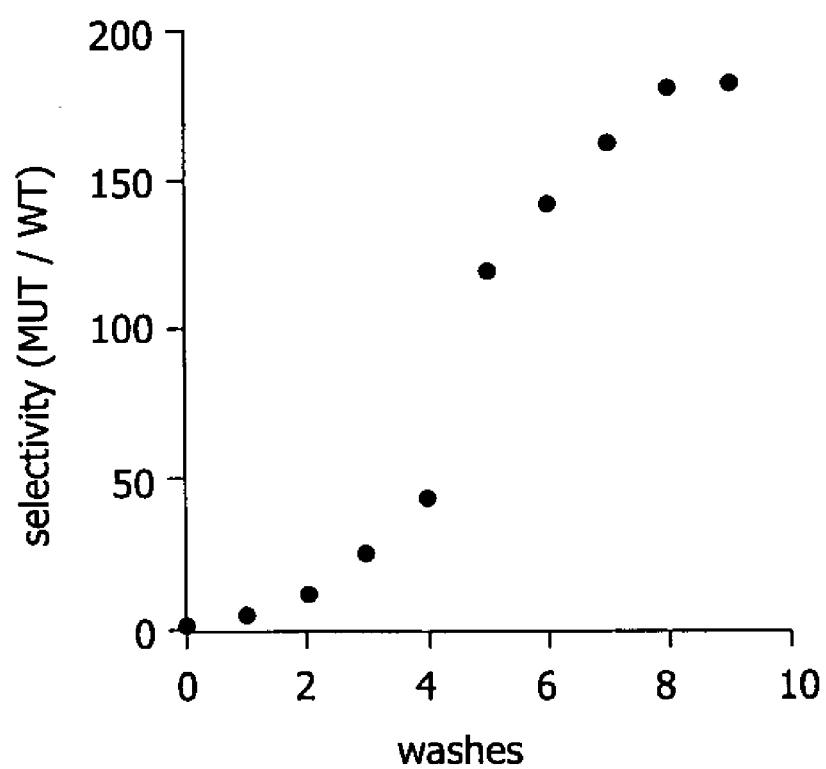

FIG. 16 depicts sequence specificity of autoligation on duplex targets in the slot-blot assay; (a) comparison of autoligation probe yields on complementary and singly mismatched targets with a single low stringency wash; (b) effect of successive SSC washes on increasing specificity of already-ligated probes; total mismatch specificity is the product of autoligation specificity and ligated probe (i.e., product) binding specificity.

Figure 17:
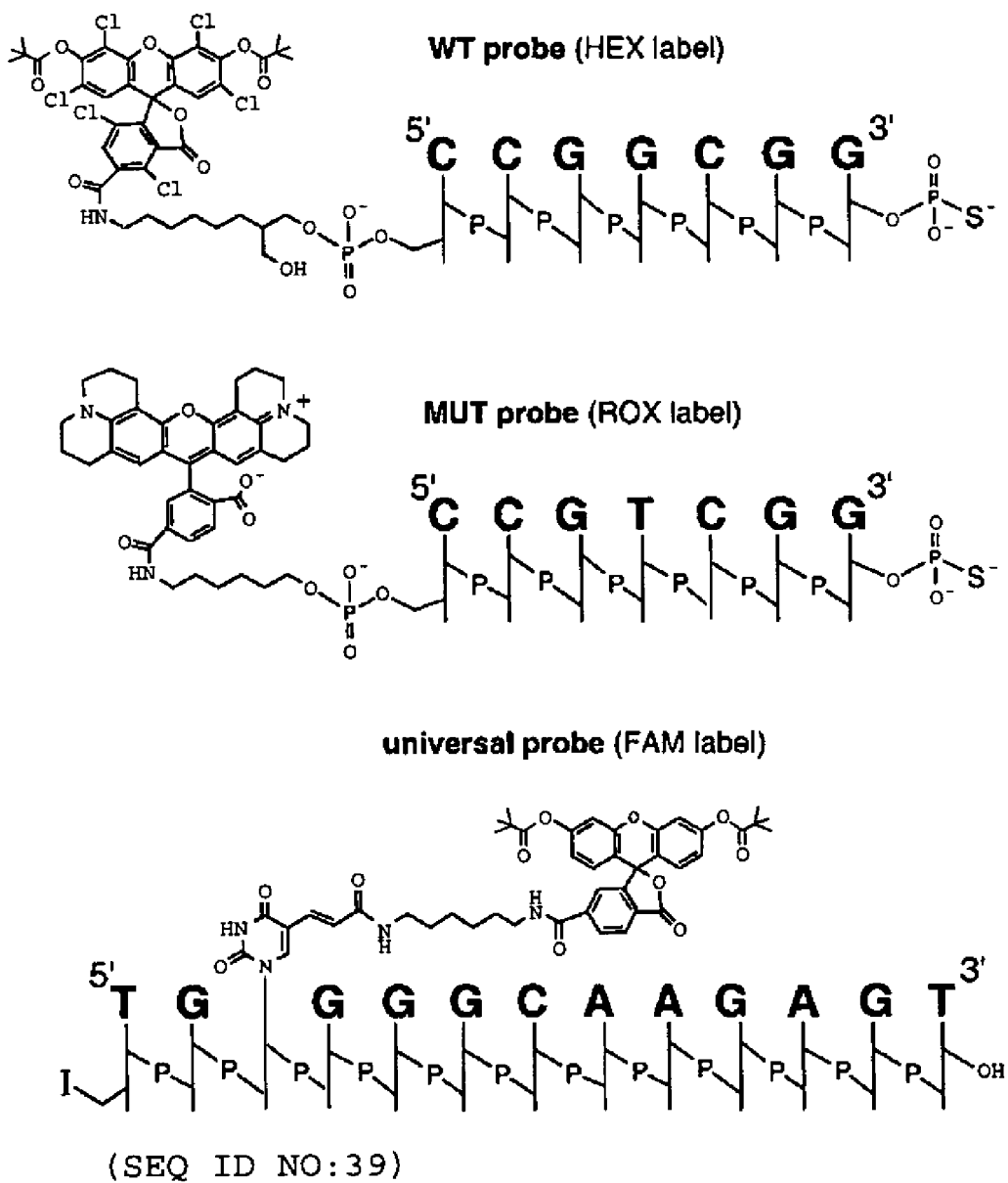

FIG. 17 shows the structures and sequences of fluorescent-labeled autoligating energy transfer (ALET) probes targeted to H-ras.

Figure 18A:
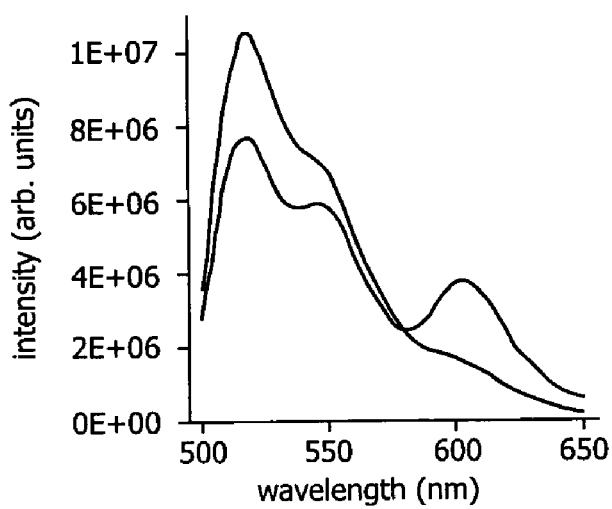
Figure 18B:
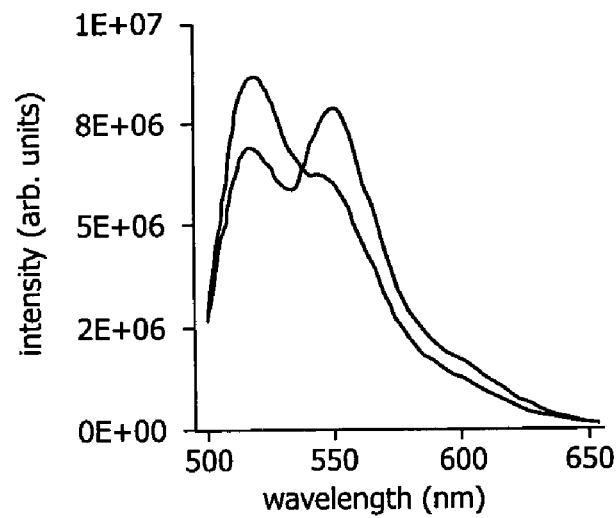
Figure 18C:
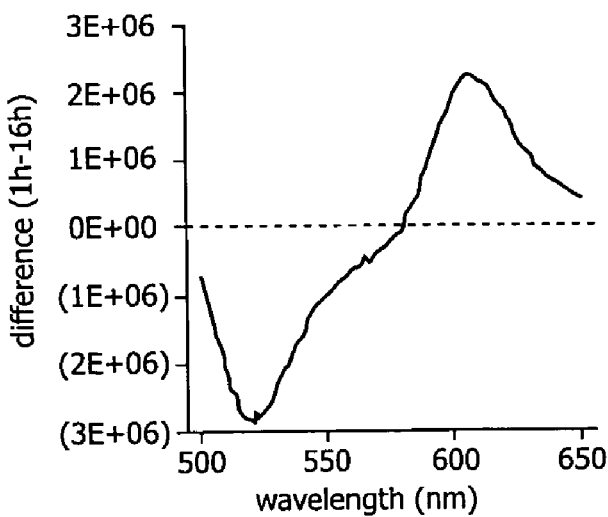

FIG. 18 depicts solution detection of H-ras sequences by ALET probes; (a) three-probe reaction with MUT DNA target; (b) three-probe reaction with WT target; (c) difference spectra (1 hour–18 hours) showing spectral changes characteristic of fluorescence resonance energy transfer; sequences are given in FIG. 17.

FIG. 19 depicts nucleotide sequences used for ligation studies in Example V; the target DNAs correspond to the H-ras gene sequence including codon 12 (E. Reddy et al., Nature, 300, 149–152 (1982)).

FIG. 20 depicts the time course of phosphoroselenoate autoligation on DNA and RNA template strands, with comparison to sulfur mediated ligations with the same sequences; lines represent fits to the early data points for initial rates analysis; conditions: 1.3 mM in each DNA strand, 10 mM MgCl$_2$, 70 mM Tris.borate (pH 7.0) at 37° C.; sequences are given in FIG. 19 (MUT targets).

Figure 21:
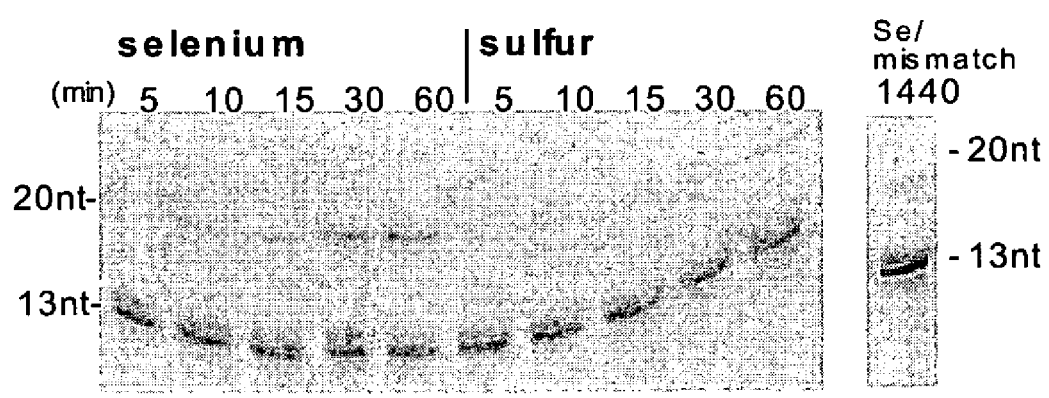

FIG. 21 depicts the time course of ligation of 7mer and 13mer probes on a DNA template (FIG. 19) using phosphoroselenoate or phosphorothioate as nucleophile.

DETAILED DESCRIPTION OF THE INVENTION

Figure 1A:
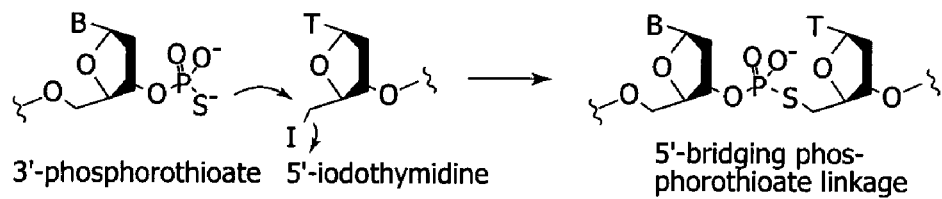
FIG. 1 depicts the chemistry of (a) sulfur-mediated and (b) selenium-mediated autoligation; in (c), "upstream" and "downstream" oligonucleotide probes, defined in relation to a polynucleotide template, are schematized.
Figure 1B:
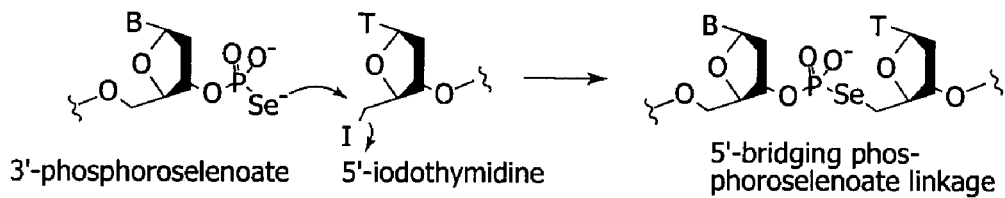

Template-directed oligonucleotide ligation is accomplished using "upstream" and "downstream" autoligating oligonucleotides that are chemically modified to ligate themselves to one another without enzymes or added reagents (see FIG. 1). In a preferred embodiment, the autoligation proceeds between an upstream oligonucleotide containing a 5' leaving group and a downstream oligonucleotide containing a phosphorothioate, phosphoroselonate or a phosphorotelluroate group, to yield a product containing a 5' bridging phosphorothioester (—O—P(O))(O$^-$)—S—), phosphoroselenoester (—O—P(O)(O$^-$)—Se—) or phosphorotelluroester (—O—P(O)(O$^-$)—Te—), as dictated by the group comprising the 3' end of the downstream oligonucleotide. The nonenzymatic oligonucleotide ligation method of the invention is useful, for example, for preparative oligonucleotide production or to detect genetic polymorphisms in DNA or RNA.

Chemically Modified Autoligating Oligonucleotides

Chemically modified autoligating oligonucleotides can contain DNA or RNA, including naturally occurring or non-naturally occurring nucleotides such as chemically or enzymatically modified nucleotides, derivatives, or analogs thereof, including peptide nucleic acid (PNA), phosphorothioate DNA, phosphorodithioate DNA, phosphoramidate DNA, amide-linked DNA, MMI-linked DNA, 2'-O-methyl RNA, alpha-DNA, methylphosphonate DNA, 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA, anhydrohexitol DNA, or DNA containing C-5 substituted pyrimidine nucleosides, C-7 substituted 7-deazapurine nucleosides, inosine nucleosides and diaminopurine nucleosides, and the like. It should be understood that, for purposes of the present invention and unless otherwise specified, the term "nucleoside" includes both 2'-deoxynucleosides (building blocks of DNA) and nucleosides (building blocks of RNA), and their derivatives and analogs, as described above. Likewise, the term "nucleotide", unless otherwise specified, includes both 2'-deoxynucleotides (building blocks of DNA) and nucleotides (building blocks of RNA), and their derivatives and analogs, as described above. An "oligonucleotide," unless otherwise specified, can includes either 2'-deoxyribonucleotides or ribonucleotides or a combination thereof. In some preferred embodiments, an oligonucleotide is a DNA oligonucleotide containing only 2'-deoxyribonucleotides, including derivatives and analogs as described above. In other preferred embodiments, an oligonucleotide is an RNA oligonucleotide containing ribonucleotides, including derivatives and analogs as described above.

Figure 1C:
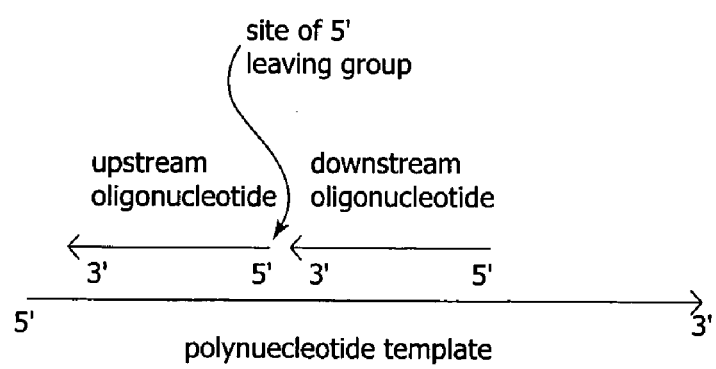
Figure 2:
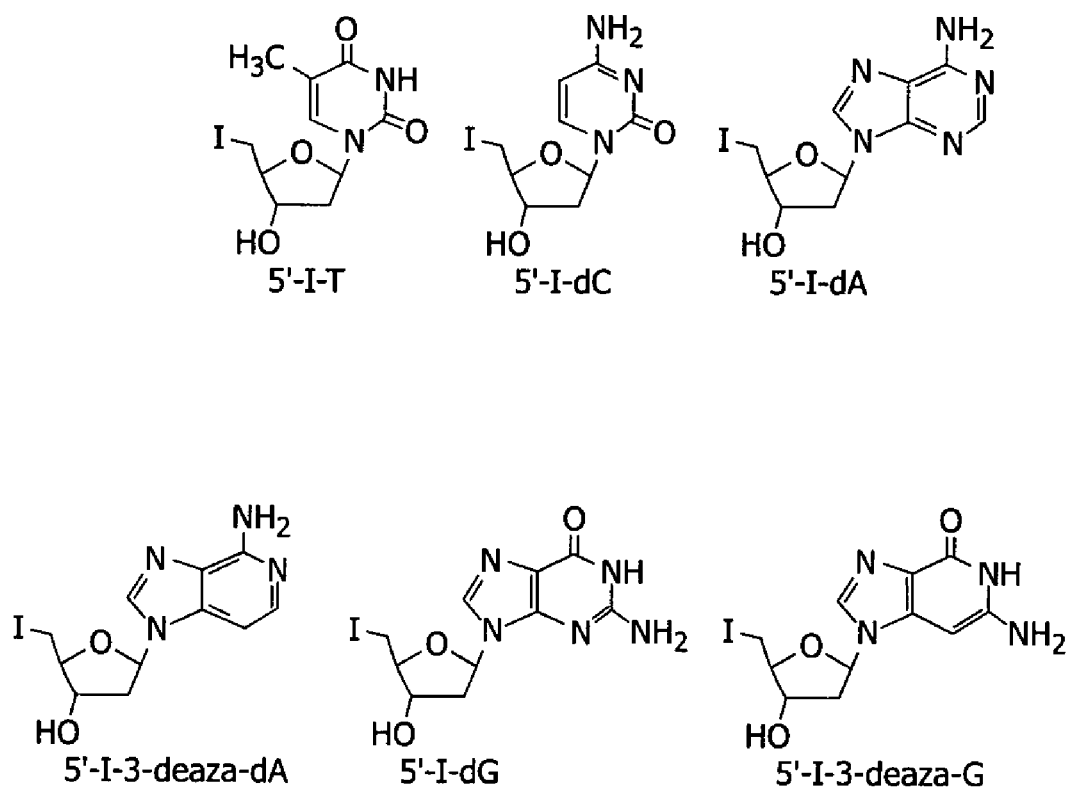
FIG. 2 depicts the structure of 5'-iodo-thymidine (5'-1-T) and variants.

The "upstream" oligonucleotide, defined in relation to the 5' to 3' direction of the polynucleotide template as the oligonucleotide that binds on the "upstream" side (i.e., the left, or 5' side) of the template (FIG. 1(c)), includes, as its 5' end, a 5'-leaving group. Any leaving group capable of participating in an S$_N$2 reaction involving sulfur, selenium, or tellurium as the nucleophile can be utilized. The leaving group is an atom or group attached to carbon such that on nucleophilic attack of the carbon atom by the nucleophile (sulfur, selenium or tellurium) of the modified phosphoryl group, the leaving group leaves as an anion. Suitable leaving groups include, but are not limited to a halide, such as iodide, bromide or chloride, a tosylate, benzenesulfonate or p-nitrophenylester, as well as RSO$_3$ where R is phenyl or phenyl substituted with one to five atoms or groups comprising F, Cl, Br, I, alkyl (C1 to C6), nitro, cyano, sulfonyl and carbonyl, or R is alkyl with one to six carbons. The leaving group is preferably an iodide, and the nucleoside at the 5' end of the upstream oligonucleotide is, in the case of DNA, a 5'-deoxy-5'-iodo-2'-deoxynucleoside. Examples of suitable 5'-deoxy-5'-iodo-2'-deoxynucleosides include, but are not limited to, 5'-deoxy-5'-iodothymidine (5'-I-T), 5'-deoxy-5'-iodo-2'-deoxycytidine (5'-I-dC), 5'-deoxy-5'-iodo-2'-deoxyadenosine (5'-I-dA), 5'-deoxy-5'-iodo-3-deaza-2'-deoxyadenosine (5'-I-3-deaza-dA), 5'-deoxy-5'-iodo-2'-deoxyguanosine (5'-I-dG) and 5'-deoxy-5'-iodo-3-deaza-2'-deoxyguanosine (5'-I-3-deaza-dG), and the phosphoroamidite derivatives thereof (see FIG. 2). In the case of RNA oligonucleotides, analogous examples of suitable 5'-deoxy-5'-iodonucleosides include, but are not limited to, 5'-deoxy-5'-iodouracil (5'-I-U), 5'-deoxy-5'-iodocytidine (5'-I-C), 5'-deoxy-5'-iodoadenosine (5'-I-A), 5'-deoxy-5'-iodo-3-deazaadenosine (5'-I-3-deaza-A), 5'-deoxy-5'-iodoguanosine (5'-I-G) and 5'-deoxy-5'-iodo-3-deazaguanosine (5'-I-3-deaza-G), and the phosphoroamidite derivatives thereof.

In a preferred embodiment, an upstream oligonucleotide contains 2'-deoxyribonucleotides except that the modified nucleotide on the 5' end, which comprises the 5' leaving group, is a ribonucleotide. This embodiment of the upstream nucleotide is advantageous because the bond between the penultimate 2'-deoxyribonucleotide and the terminal 5' ribonucleotide is susceptible to cleavage using base. This allows for potential reuse of an oligonucleotide probe that is, for example, bound to a solid support, as described in more detail below.

The "downstream" oligonucleotide, which binds to the polynucleotide template "downstream" of, i.e., 3' to, the upstream oligonucleotide, includes, as its 3' end, a nucleoside having linked to its 3' hydroxyl a phosphorothioate group (i.e., a "3'-phosphorothioate group"), a phosphoroselenoate group (i.e., a "3'-phosphoroselenoate group), or a phosphorotelluroate group (i.e., a "3'-phosphorotelluroate group"). The chemistries used for autoligation are thus sulfur-mediated, selenium-mediated, or tellurium mediated. Self-ligation yields a ligation product containing a 5' bridging phosphorothioester (—O—P(O)(O$^-$)—S—), phosphoroselenoester (—O—P(O)(O$^-$)—Se—) or phosphorotelluroester (—O—P(O)(O$^-$)—Te—), as dictated by the group comprising the 3' end of the downstream oligonucleotide. This non-natural, achiral bridging diester is positioned between two adjacent nucleotides and takes the place of a naturally occurring 5' bridging phosphodiester. Surprisingly, the selenium-mediated ligation is 3–4 times faster than the sulfur-mediated ligation, and the selenium-containing ligation product was very stable, despite the lower bond strength of the Se—P bond. Further, the bridging phosphoroselenoester, as well as the bridging phosphorotelluroester, are expected to be cleavable selectively by silver or mercuric ions under very mild conditions (see M. Mag et al., Nucleic Acids Res., 19, 1437–1441 (1991)).

In a preferred embodiment, an downstream oligonucleotide contains 2'-deoxyribonucleotides except that the modified nucleotide on the 3' end, which comprises the 3' phosphorothioate, phosphoroselenoate, or phosphorotelluroate, is a ribonucleotide. This embodiment of the upstream nucleotide is advantageous because the bond between the penultimate 2'-deoxyribonucleotide and the terminal ribonucleotide is susceptible to cleavage using base, allowing for potential reuse of an oligonucleotide probe that is, for example, bound to a solid support.

It should be noted that the "upstream" and "downstream" oligonucleotides can, optionally, constitute the two ends of a single oligonucleotide, in which event ligation yields a circular ligation product. The binding regions on the 5' and 3' ends of the linear precursor oligonucleotide must be linked by a number of intervening nucleotides that is sufficient to allow binding of the 5' and 3' binding regions to the polynucleotide target.

Compositions provided by the invention include a 5'-deoxy-5-'iodo-2'-deoxynucleoside, for example a 5'-deoxy-5'-iodothymidine (5'-I-T), 5'-deoxy-5'-iodo-2'-deoxycytidine (5'-I-dC), 5'-deoxy-5'-iodo-2'-deoxyadenosine (5'-I-dA), 5'-deoxy-5'-iodo-3-deaza-2'-deoxyadenosine (5'-I-3-deaza-dA), 5'-deoxy-5'-iodo-2'-deoxyguanosine (5'-I-dG) and 5'-deoxy-5'-iodo-3-deaza-2'-deoxyguanosine (5'-I-3-deaza-dG), and the phosphoroamidite derivatives thereof, as well as an oligonucleotide comprising, as its 5' end, a 5'-deoxy-5'-iodo-2'-deoxynucleoside of the invention. Compositions provided by the invention further include a 5'-deoxy-5'-iodonucleoside such as 5'-deoxy-5'-iodouracil (5'-I-U), 5'-deoxy-5'-iodocytidine (5'-I-C), 5'-deoxy-5'-iodoadenosine (5'-1-A), 5'-deoxy-5'-iodo-3-deazaadenosine (5'-I-3-deaza-A), 5'-deoxy-5'-iodoguanosine (5'-I-G) and 5'-deoxy-5'-iodo-3-deazaguanosine (5'-I-3-deaza-G), and the phosphoroamidite derivatives thereof, as well as an oligonucleotide comprising, as its 5' end, a 5'-deoxy-5'-iodonucleoside of the invention. Also included in the invention is a nucleoside comprising a 3'-phosphoroselenoate group or a 3'-phosphorotelluroate group, and an oligonucleotide comprising as its 3' end a nucleoside comprising a 3'-phosphoroselenoate group or a 3'-phosphorotelluroate group. Oligonucleotides containing either or both of these classes of modified nucleosides are also included in the invention, as are methods of making the various nucleosides and oligonucleotides. Oligonucleotides that are modified at either or both of the 5' or 3' ends in accordance with the invention optionally, but need not, include a detectable label, preferably a radiolabel, a fluorescence energy donor or acceptor group, an excimer label, or any combination thereof.

Template or Target Polynucleotide

In methods directed to oligonucleotide synthesis, the oligonucleotide or polynucleotide to which the two chemically modified autoligating oligonucleotides bind is sometimes referred to herein as the "template" oligonucleotide or polynucleotide. In methods directed to detection of mutations in a nucleic acid, the oligonucleotide or polynucleotide to which the two chemically modified auto-ligating oligonucleotides bind is sometimes referred to herein as the "target" oligonucleotide or polynucleotide. It should be understood that the terms "oligonucleotide" and "polynucleotide," as used herein interchangeably. It should be further understood that the general term "template-directed" auto-ligation is meant to include the self-ligation of two chemically modified auto-ligating oligonucleotides that are bound to a third oligonucleotide substantially adjacent to each other, regardless of whether the third oligonucleotide is referred to as a "template" oligonucleotide or polynucleotide, a "target" oligonucleotide or polynucleotide, or by any other descriptive term.

The template or target polynucleotide can be single-stranded or double stranded, and can be RNA or DNA. It can be a synthetic polynucleotide or a naturally occurring oligonucleotide, without limitation. If naturally occurring, the target polynucleotide is typically isolated from a biological sample such as a cell, bodily fluid or tissue.

Autoligation

The chemically modified autoligating oligonucleotides bind to a polynucleotide template or target substantially adjacent to each other. Oligonucleotides bind to a template or target polynucleotide "substantially adjacent" to each other when the 5' end of the "upstream" nucleotide binds to a base on the template or target polynucleotide that is directly adjacent to (see FIG. 1), or within 2 bases either side of, preferably within about 1 base either side of, a base on the template or target polynucleotide bound by the 3' end of the "downstream" nucleotide. The term "substantially adjacent" thus includes, for example, oligonucleotides that are bound to the template or target polynucleotide directly adjacent to each other; oligonucleotides bound to the template or target polynucleotide such that there is a gap of 1 or 2 bases between the "upstream" and "downstream" oligonucleotide; and oligonucleotides bound to the template or target polynucleotide such that there is a 1 or 2 nucleotide overlap between the two oligonucleotides.

When bound to a polynucleotide template or target substantially adjacent to each other, the upstream and downstream oligonucleotides self-ligate due to their close proximity and the presence of reactive groups on their adjacent ends. Chemically modified oligonucleotides that bind to a template or target polynucleotide directly adjacent to each other are, of course, preferred, but the method of invention is by no means limited to directly adjacent binding.

Preparative Oligonucleotide Synthesis

The method of the invention can be used to construct oligonucleotides that are too large to be synthesized in a single chain. To construct a large oligonucleotide, a polynucleotide template is designed to serve as a "splint" having adjacent regions that are complementary to the 5' end of one constituent oligonucleotide and the 3' end of the other constituent nucleotide so as to bring the 3' and 5' ends of the constituent oligonucleotides in close proximity to allow autoligation according to the method. Two or more oligonucleotides can be contacted to the splint simultaneously; in methods where three or more constituent oligonucleotides are used, oligonucleotides occupying middle positions will include both a 5' leaving group and a 3' phosphoroselenoate, phosphorotelluroate, or phosphorothioate group, depending on the ligation chemistry employed. Using this method, large DNAs can be generated for use in, for example, in vitro transcription. Synthetic genes can also be constructed. Likewise, an polynucleotide "splint" having adjacent regions that are complementary to the 5' end and the 3' ends of a single linear oligonucleotide can be used to circularize the linear oligonucleotide via autoligation of its 5' and 3' ends.

It should be noted that oligonucleotides containing a 5' bridging phosphoroselenoester or phosphorotelluroester were unknown until the present invention and are thus encompassed within the invention.

Detection of Genetic Polymorphisms

Genetic polymorphisms include, but are not limited to, one or more single nucleotide polymorphisms (SNPs, also known as point mutations), insertions, deletions, translocations, or larger rearrangements of genetic material, such as DNA or RNA. In one embodiment of the invention, upstream and downstream oligonucleotides are designed to bind to a target polynucleotide suspected of containing the polymorphism, such that they are substantially adjacent to each other and thereby amenable to autoligation. As described above, the upstream oligonucleotide contains, at its 5' end, the 5' leaving group, while the downstream oligonucleotide contains, at its 3' end, the nucleophile (i.e., the phosphorothioate, phosphoroselenoate, or phosphorotelluroate); binding of the oligonucleotides to the target polynucleotide allows self-ligation to occur between the 5' end of the upstream oligonucleotide and the 3' end of the downstream oligonucleotide, producing a single linear ligation product (or, if the upstream and downstream oligonucleotides are a single oligonucleotide, a circular ligation product). Typically the method for detecting genetic polymorphisms utilizes one "universal" oligonucleotide and two or more "polymorphism" oligonucleotides, one of which is a wild-type oligonucleotide used as a control. If the universal oligonucleotide is the upstream oligonucleotide, the polymorphism oligonucleotides(s) are the downstream oligonucleotides; alternatively, if the universal oligonucleotide is the downstream oligonucleotide, the polymorphism oligonucleotide(s) are the upstream oligonucleotides. It is also within the scope of the invention that the polymorphism oligonucleotide(s) are flanked by two universal oligonucleotides on a single polynucleotide target, or, alternatively, that two polymorphism oligonucleotides (detecting different mutations) flank a single universal oligonucleotide. The use of multiple universal oligonucleotides and polymorphism oligonucleotides in a single detection method, either simultaneously or serially, is likewise contemplated.

The "universal oligonucleotide" binds to both the wild-type and mutant polynucleotide target, either 5' (in the case of an upstream oligonucleotide) or 3' (in the case of a downstream oligonucleotide) to the site of the genetic polymorphism. The universal oligonucleotide is preferably about 6 to about 100 nucleotides in length, more preferably about 10 to about 30 nucleotides in length. It is preferably about 80% to about 100% complementary to the polynucleotide target; more preferably it is 100% complementary to the target. The "wild-type" polymorphism oligonucleotide has a nucleotide sequence that is preferably 100% complementary to a sequence in the wild-type polynucleotide target, such that it binds to the wild-type target substantially adjacent to the universal oligonucleotide. A "mutant" polymorphism oligonucleotide binds the analogous location in the mutated polynucleotide target, and has a nucleotide sequence that is preferably 100% complementary to a sequence in the mutant polynucleotide target, such that it binds to the mutant target substantially adjacent to the universal oligonucleotide. Where a single nucleotide polymorphism (SNP) is being detected, the wild-type and mutant polymorphism oligonucleotides, if they are the same length, will differ by only a single base, at the site of the point mutation. An oligonucleotide probe of the invention is preferably between about 3 and about 12 nucleotides in length, more preferably between about 4 and about 8 nucleotides in length. Significantly, this process allows very short SNP oligonucleotide probes to be used, e.g. those of 3, 4, 5, and 6 nucleotides in length. The mutant and wild-type polymorphism oligonucleotide probes may be the same length or they can differ in length. The site of the genetic polymorphism, in this case the point mutation, is preferably near the middle of the mutant polymorphism oligonucleotide, although it may alternatively be at or near the ligation junction end. Where two closely positioned SNPs are being detected, mutant oligonucleotide probes can be designed that contain either one or both of the point mutations, and will differ from the wild-type polymorphism oligonucleotide probe accordingly. Where genetic rearrangements are being detected, the wild-type and mutant polymorphism probes may have no sequence identity at all.

The mutant oligonucleotide probe having a nucleotide sequence complementary to the mutant target will selectively self-ligate with the universal oligonucleotide probe in a template-directed, nonenzymatic ligation in the presence of a mutant polynucleotide target, whereas the wild-type polymorphism oligonucleotide probe having a nucleotide sequence complementary to the wild-type target will selectively self-ligate in the presence of a wild-type polynucleotide target. Preferably, at least one of the oligonucleotide probes is detectably labeled so that at least one of the ligation products is thereby labeled, although ligation events also can be detected using PCR, rolling circle amplification, gel electrophoresis or the like without detectably labeling the ligation products.

The presence or absence of a labeled ligation product can be used to detect a genetic polymorphism in various ways. For example, the target polynucleotide can be contacted with the universal oligonucleotide probe and a mutant polymorphism oligonucleotide probe, one of which is labeled, to determine whether a ligation product is produced (indicating the presence of a point mutation) and/or the target polynucleotide can be contacted with the universal oligonucleotide probe and the wild-type polymorphism oligonucleotide probe, at least one of which is labeled, to determine whether a ligation product is produced (indicating the absence of a point mutation). Preferably, the target polynucleotide is contacted with three or more oligonucleotide probes simultaneously (i.e., the universal probe, the wild-type polymorphism probe, and at least one mutant polymorphism probe) such that the mutant and wild-type polymorphism probes compete for binding to the polynucleotide template. One of the mutant or wild-type polymorphism probes is preferably radiolabeled, such that the presence of a ligation product can be associated with either the wild-type or mutant genotype. Alternatively or in addition, the oligonucleotide probes are fluorescently labeled such that a ligation event is accompanied by a change in color upon excitation, due to a transfer of energy from a fluorescence energy donor on one probe to a fluorescence energy acceptor on the probe to which it is ligated. In a particularly preferred embodiment of the invention, the fluorescent labels are selected such that ligation of the mutant probe to the universal probe is associated with one color change, and ligation of the wild-type polymorphism probe to the universal probe is associated with a color change that is different from the color change that characterizes the mutant-universal probe ligation, as discussed in more detail below. It should be understood that the ligation reactions are conducted under conditions that allow selective binding of the mutant polymorphism probe or the wild-type polymorphism probe, which in many cases will differ by only one nucleotide, to the target polynucleotide.

The nonenzymatic oligonucleotide ligation method of the invention is thus very useful for detection and identification of suspected point mutations (single nucleotide polymorphisms) in a 1: polynucleotide target, for example in patient samples as a method of diagnosis or genetic screening. It is also useful in medical diagnostic methods such as ligation-mediated polymerase chain reaction (PCR) and padlock probe ligation. With respect to existing padlock probe technology, the method of the present invention utilizes chemistry that obviates the need for an enzyme. Reagents for use in practicing the method of the present invention, for example to detect known genetic mutations in human genetic material associated with cancer or other disease, can be conveniently packaged as a kit for use in medical or laboratory diagnostics or screening. The non-natural sulfur linkages (and, by extension, the non-natural selenium or tellurium linkages) introduced in the ligation does not hinder the activity of polymerases, implying that technologies such as rolling-circle amplification (U.S. Pat. No. 5,714,320, Kool) can be used for the formation of padlock probes and other ligase-mediated diagnostic methods. Like ligase-based methods, the present method is highly selective against point mutations in the polynucleotide target at or near the ligation junction.

In addition to detection of point mutations, the method of the invention can be used to detect deletions, insertions, and translocations of genetic material. Detection of specific RNAs and viruses, including identification of mutants, can also be accomplished. The method of the invention is also readily adaptable to use in high-density arrays for genetic screening and pharmocogenomics. For example, it is useful to detect point mutations in genes that are associated with, or causative of, pancreatic and colon cancer. Also, the method can be used to stain RNAs in tissues and cells.

As noted above, at least one of the oligonucleotide probes is, optionally, detectably labeled to facilitate detection of the ligation product. The detectable label can be a radiolabel, a fluorescent label, a chemical label, an enzymatic label, an affinity label, or the like. Additionally, the method of the invention was found under certain conditions to be capable of self-amplification of the signal provided by the detectable label; in some instances, the ligated product may dissociate from the target polynucleotide template, leaving the target open for more unligated oligonucleotide probes to bind and be ligated.

The present method of genetic polymorphism detection has a number of advantages over enzymatic (ligase-based) detection methods and over other existing methods based on chemical ligation. Ligase-based detection methods work only on DNA targets, since formation of a DNA—DNA duplex is critical to the functioning of the ligase; however the present method can be used to probe (e.g., detect mutations in) RNA sequences as well as DNA sequences. Moreover, the method of the present invention appears to be more sequence-specific than all known methods for SNPS detection other than enzymatic method using Tth ligase. Because it involves autoligation of the oligonucleotides, it requires no enzymes or reagents, reducing cost and simplifying the process. This feature also allows use of the method in situ, such as inside intact cells or tissues. Since it is nonenzymatic, the present method can also be used in other biological and nonbiological environments, such as cell extracts or media, denaturing solvents, or the like, in which ligases can not function effectively. Finally, unlike many other chemical ligations, the method of the invention produces ligation junctions which can be replicated by polymerases, allowing post-ligation amplification of the ligated oligonucleotide using standard techniques, such as PCR, if desired.

Ligation of fluorescently labeled oligonucleotides can be advantageously detected in solution or cell extracts using fluorescence spectroscopy, or in whole cells using fluorescence microscopy, or fluorescence-based cell sorting techniques, such as flow-assisted cell sorting (FACS). Fluorescence can also be detected in gels and blots under ultraviolet light. In this embodiment of the invention, one oligonucleotide is modified so as to contain a fluorescence energy donor group, and a second oligonucleotide is modified to contain a fluorescence energy acceptor group. Successful ligation is detectable by a change in color. Upon ligation of the two oligonucleotides, the donor and acceptor groups are placed in sufficiently close proximity for energy transfer to occur.

Enzymatic Ligation on a Solid Support

The preparative and diagnostic methods of the present invention can advantageously be adapted for use on a solid support, such as a column or a chip. One or more oligonucleotide probes is conjugated to a support, preferably at the end opposite of the end containing the functional group that participates in the ligation reaction. In a particularly preferred embodiment, the ligation product is cleavable such that the conjugated oligonucleotide probes can be reused. To facilitate this aspect of the invention, an oligonucleotide probe can contain 2'-deoxyribonucleotides except that the modified nucleotide on the ligating end, which comprises the functional group that participates in ligation, is a ribonucleotide. Either the oligonucleotide comprising the 5' leaving group or the oligonucleotide comprising the 3' functional group (i.e., the 3' phosphorothioate, phosphoroselenoate or phosphorotelluroate), or both, can include the terminal, modified ribonucleotide. As noted above, the bond between a 2'-deoxyribonucleotide and a ribonucleotide) susceptible to cleavage using base. This allows for potential reuse of the conjugated oligonucleotide probe.

Autoligating Energy Transfer (ALET) Oligonucleotides

In a particularly advantageous embodiment of the non-enzymatic ligation method of the invention, autoligating fluorescence resonance energy transfer oligonucleotides can be employed to detect genetic polymorphisms in a target polynucleotide. In a preferred embodiment of this aspect of the invention, the universal oligonucleotide probe contains a fluorescence energy donor group, such as fluorescein, and one or more of the polymorphism oligonucleotide probes contain a fluorescence energy acceptor group, such as tetramethylrhodamine (ROX) or hexachlorofluorescein (HCF); alternatively, the universal oligonucleotide probe can contain a fluorescence energy acceptor group while at least of the polymorphism oligonucleotide probes contains a fluorescence energy donor group. For example, an universal oligonucleotide probe can contain fluorescein, a wild-type polymorphism oligonucleotide probe can contain ROX, and a mutant polymorphism oligonucleotide probe can contain HCF. An unligated mixture of all three probes yields green fluorescence when subjected to short wavelengths (about 400 nm to about 500 nm) chosen to selectively excite fluorescein. Ligation of the mutant oligonucleotide to the universal oligonucleotide is accompanied by a color change from green to red (energy transfer from fluorescein to ROX) indicating the presence of the point mutation in the polynucleotide template. Ligation of the wild-type oligonucleotide to the universal oligonucleotide, on the other hand, is accompanied by a color change from green to yellow (energy transfer from fluorescein to HCF), indicating the absence of the point mutation in the polynucleotide template.

Alternatively, genetic polymorphisms in a polynucleotide template can be detected using fluorescently labeled universal and mutant polymorphism oligonucleotide probes without labeling the wild-type polymorphism oligonucleotide probe. Also, it should be noted that multiple mutant polymorphism probes can be used to detect multiple mutations in a polynucleotide template, each probe containing a different fluorescence energy transfer group such that each possible ligation event is individually detectable using the appropriate excitation wavelengths coupled with monitoring of the fluorescence emission spectrum. It should further be noted that changes in fluorescence emission can be detected while the autoligated oligonucleotide product is still hybridized to the polynucleotide template or target; it is not necessary that it dissociate therefrom.

The autoligating energy transfer (ALET) ligation method of the invention has an advantage over other energy transfer strategies of "locking in" the result by covalent joining of the oligonucleotides harboring the two dyes. This means that the signal will remain under any conditions, even denaturing conditions. It should, of course, be understood that the ALET method of the invention is not intended to be limited to the use of any particular dye color combination or fluorophore.

The ligation method of the invention can also be used to ligate pyrene-containing upstream and downstream oligonucleotides as described herein, wherein the upstream oligonucleotide contains, as its 5' end, a pyrene nucleoside such as a 5'-iodopyrene (Paris et al., *Nucleic Acids Research* 26:3789–3793 (1998)), and the downstream oligonucleotide contains, as its 3' end, a pyrene nucleoside having a 3'-phosphorothioate, a 3'-phosphoroselenoate, or a 3' phosphorotelluroate. Joining of the pyrene moieties yields efficient excimer which is not eliminated by denaturation. Moreover, pyrene excimers are expected to serve as good donors for energy transfer. Therefore, as an alternative to fluorescence resonance energy transfer (FRET) to effect the color changes, excimer resonance energy transfer (ERET) can be used in combination with the fluorescence energy transfer in accordance with the autoligation method of the invention by using oligonucleotide probes comprising pyrene excimers.

Ligation Products Containing Phosphorylacetylamino Bonds

The invention is not intended to be limited to ligation products containing achiral phosphoroester linkages. For example, in an alternative embodiment of the invention, the autoligation proceeds between an upstream oligonucleotide containing an α-haloacyl group, such as an α-haloacetylamino group, and a downstream oligonucleotide containing a phosphoroselenoate or a phosphorotelluroate group product to yield a product containing a 5' bridging selenophosphorylacetylamino or tellurophosphorylacetylamino group. See U.S. Pat. No. 5,476,930 (Letsinger et al.) for a list of suitable α-haloacyl groups. In another embodiment, autoligation of an upstream oligonucleotide containing an α-haloacyl group, such as an α-haloacetylamino group, and a downstream oligonucleotide containing a phosphorothioate, phosphoroselenoate or a phosphorotelluroate group proceeds on an RNA template to yield a product containing a 5' bridging selenophosphorylacetylamino, selenophosphorylacetylamino or tellurophosphorylacetylamino group.

The present invention is illustrated by the following examples. It is to be understood that the particular examples, materials, amounts, and procedures are to be interpreted broadly in accordance with the scope and spirit of the invention as set forth herein.

EXAMPLES

Example I

Figure 3:
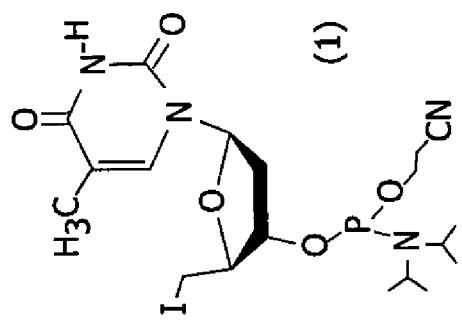
FIG. 3 shows the synthesis of the iodophosphoroamidite of thymidine.
Figure 3:
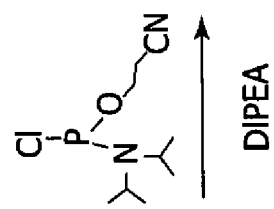
Figure 3:
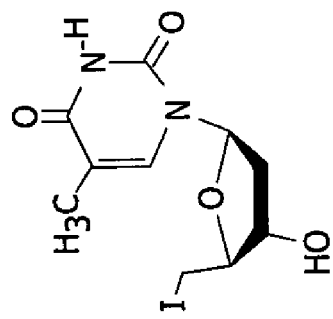
Figure 3:
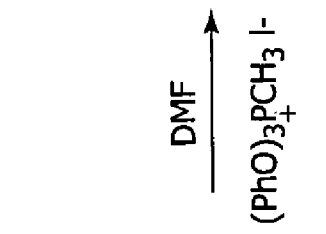
Figure 3:
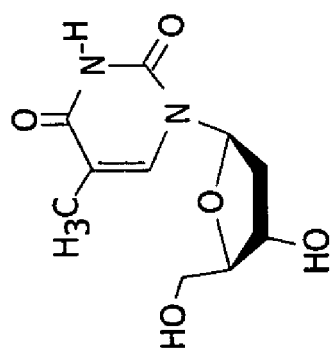

Novel 5'-Iodonucleoside Allows Efficient Nonenzymatic Ligation of Single-stranded and Duplex DNAs Synthesis and Stability of 5'-iodo-thymidine The iodophosphoramidite of thymidine (1) was synthesized in only two steps and in straightforward fashion (FIG. 3). Iodination of thymidine was performed according to the method of Verheyden et al. (J. Org. Chem., 35, 2319 (1970)) and subsequent phosphitylation proceeded normally to yield the iodide (1), suitable for automated DNA synthesis. Incorporation into oligonucleotides was carried out using the standard coupling cycle. Intact incorporation into DNA proceeded in ~85–95% yield, and was confirmed by HPLC analysis of oligonucleotide products, which have slower mobility on a reverse-phase column when iodinated. Analysis showed one major product (monitoring at 260 nm) and only minor amounts of non-coupled (n−1)mer product, as confirmed by coinjection with authentic samples.

The stability of the 5'-iodothymidine in comparison to the 5'-tosylthymidine was analyzed by thin layer chromatography under varied conditions. Results showed that the tosylnucleoside in concentrated ammonia (55° C.) has a half-life of less than 1 hour, whereas the iodonucleoside has a half-life of about 7 hours. When treated at room temperature for 24 hours (conc. $NH_3$) the tosylnucleoside is >90% degraded, while the iodonucleoside is <2% degraded. The stability of the iodide in oligonucleotides was also analyzed by reverse-phase HPLC. Chromatograms revealed that the iodide (in the sequence

```
5'-I-TTCACGACGCCTG)         (SEQ ID NO: 3)
``` has a half-life of >4 days in conc. $NH_3$ at 23° C., similar to that of the nucleoside alone. Based on the HPLC analysis we chose the following conditions for deprotection: concentrated ammonia, 55° C. for 1 hour, followed by incubation at room temperature for 23 hours, or treatment at room temperature alone for 24 hours. It is anticipated that the iodide would also be stable to rapid deprotection conditions, although this was not explicitly tested.

Template-Directed Oligonucleotide Ligation

The ability of 5'-iodo-oligonucleotides to undergo template-directed ligations (as in FIG. 1(a)) was also examined. Previous studies used the tosylnucleoside strategy to close self-templated dumbbell structures and to ligate a synthetic "cap" to close a hairpin structure. Our own goals involved the ligation of single-stranded oligonucleotides (using a complementary "splint") to yield longer sequences, ligation of duplexes, and cyclization of oligonucleotides, also using a short splint sequence. We therefore examined three different ligation reactions on preparative scales: ligation of two short (8mer+12mer) oligonucleotides using an 18mer splint, one-pot ligation of 30+33mers (20mer splint) followed by cyclization to yield a 63mer circular DNA, and dimerization-ligation of self-complementary 28mer hairpin duplexes having 4-base overhanging "sticky" ends. The sequences tested, expected products are shown in FIG. 4 (a).

Figures 4A, 4B:
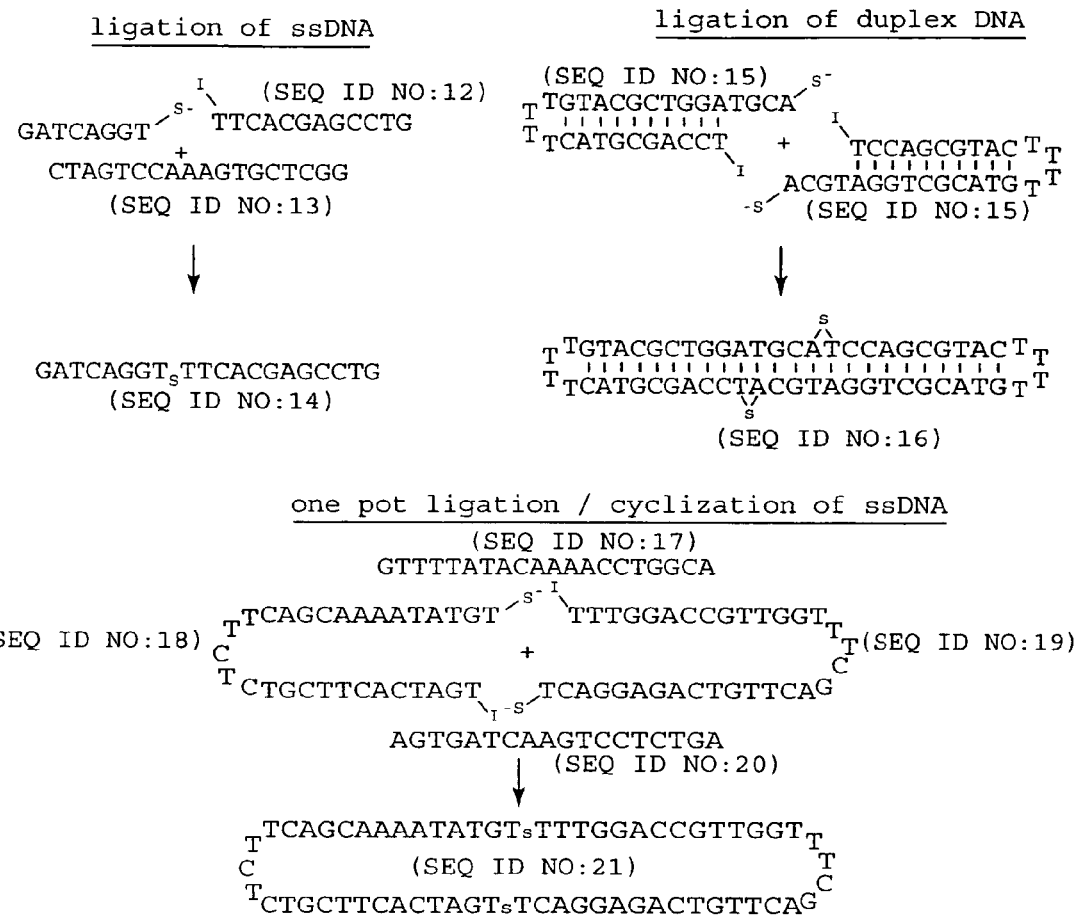
FIG. 4 shows (a) the starting sequences and product sequences in the three types of ligations described in Example I and (b) preparative yields for the three typed of ligations.

Also required for ligations are 3'-phosphorothioate groups, which were incorporated as described in Herrlein et al. (J. Am. Chem. Soc., 117, 10151(1995)). The standard conditions used for ligations were: 10 mM $MgCl_2$, 10 mM Tris.acetate (pH 7.0), 23° C., and a DNA concentration of 50 μM for intermolecular reactions or 1.3 μM for intramolecular reactions. Splint concentrations were 1.1 times that of the DNAs being ligated. The results were analyzed by denaturing gel electrophoresis. A time course of the simple ligation showed that it proceeds over a period of 12–18 hours and reaches a plateau of about 90% ligation after about 18 hours. The preparative reactions were carried out on 20–50 nmole scales over 18 hours using crude, unpurified starting materials and the products were isolated by preparative electrophoresis. Reaction conversions and isolated yields are shown in FIG. 4(b). In general, the ligation is found to proceed quite well, with apparent conversions (as judged by UV shadowing of the preparative gels) of ca. 45–95%, and isolated yields ranging from 20% for the combined two-step ligation and cyclization to 44% for the simple ligation. The one-pot two-step reaction was carried out using only the top splint in the first step; after 18 hour (room temperature) the reaction was diluted with buffer to lower the strand concentration to 1.3 μM, and the second splint was added. After another 18 hours the reaction was worked up and the products isolated. The cyclic product was distinguished from undesired dimer by treatment with S1 nuclease (S. Wang et al., Nucleic Acids Res., 23, 1157 (1995)). Although the same reactions were not compared, it appears that ligation rates may be somewhat slower for the less reactive iodide than for a tosylate; however, both methods appear to give quite high ligation yields.

The results thus showed that a 5'-iodide can be conveniently incorporated into DNA oligonucleotides in a thymidine derivative, and that the reactive group undergoes little or no degradation under standard conditions of synthesis and deprotection. Reacting an oligonucleotide having as a leaving group a 5'-iodo group with an oligonucleotide having a 3' phosphorothioate group gave good ligation yields and, because of the stability of the iodide, allowed the use of standard deprotection methods. This makes possible several practically useful template-directed ligations, including the ligation of ssDNAs, cyclization of ssDNAs, and ligation of sticky-ended duplexes. These reactions proceed in good yield and without specialized protecting groups or deprotection conditions. The method further obviates the need for ligase enzyme, which is costly on a preparative scale.

Example II

Chemical and Enzymatic Properties of Bridging 5'-S-Phosphorothioester Linkages in DNA Introduction Strategically placed sulfur atoms have found widespread utility in the probing of specific interactions of proteins, enzymes, and metals with nucleic acids. Replacements of sulfur for oxygen in the sugar-phosphate backbone of DNA and RNA have been central to many mechanistic studies of bond cleavage reactions. For example, much work has been carried out with sulfur replacing specific non-bridging phosphate oxygens in DNA and RNA, which has led to important insights into enzymatic and RNA-catalyzed cleavage of phosphodiesters in several classes of molecules. Sulfur replacements for oxygen have also been carried out at the 2' position of RNA and in the 3' and 5' positions of RNA and of DNA. These last two positions are termed "bridging" positions in the phosphate linkage, and these positions are important because they can make specific interactions with proteins or metals and because they act as leaving groups in various catalyzed RNA or DNA cleavage reactions.

Recent work has focused on the properties of the 5' bridging sulfur in the context of RNA, in part because of its relevance to enzymatic and RNA-catalyzed cleavage reactions. This sulfur replacement is useful as a mechanistic probe, and it is especially labile to hydrolysis because it presents the already-labile RNA linkage with a better leaving group. This property results in about a $10^6$-fold increase in its ease of hydrolysis at neutral pH.

The analogous 5' bridging sulfur in DNA is considerably less well studied as a mechanistic probe. While a number of synthetic methods have been investigated for creating such a linkage, very few studies of chemoenzymatic properties of this structure exist. Although it has been shown that silver nitrate and other chemical reagents can cleave this linkage specifically (M. Mag et al., Nucleic Acids Res. 19, 1437–1441 (1991)), we are aware of only two studies which investigate enzyme-DNA interactions. One report studied a dinucleotide containing a 5'-bridging sulfur, and it was reported that phosphodiesterases from calf spleen and snake venom were able to cleave this linkage, but without reference to rate or comparison with the natural DNA linkage (A. Cook, J. Am. Chem. Soc. 92, 190–195 (1970)). A second study investigated dT oligomers completely substituted with 5' bridging sulfur (V. Rybakov et al., Nucleic Acids Res. 9, 189–201 (1981)), and it was found that the exonuclease of T4 DNA polymerase and Snake Venom Phosphodiesterase (SVPDE) showed significantly reduced ability to cleave such oligomers. Thus, little detailed work has been focused on this linkage and importantly, no studies have examined the hydrolytic stability of this linkage, the effect of isolated 5'-S linkages on duplex stability, or whether this linkage can act as a substrate for either restriction endonucleases or polymerase enzymes.

In this Example, the 5'-S linkages were found to be stable for extended periods in aqueous buffers and to be resistant to some, but not all, exonuclease enzymes. A restriction endonuclease was strongly inhibited in cleaving bonds adjacent to the P—S bonds, although singly-placed 5' bridging sulfurs are found to cause only small thermal destabilization of duplexes. Surprisingly, DNAs with 5'-S linkages were found to act as normal templates for DNA and RNA polymerases. The chemical stability and surprisingly small perturbation by the 5'-bridging sulfur suggest that an oligonucleotide containing a phosphorothioester linkage will be very useful as a physical and mechanistic probe for specific protein or metal interactions involving this position in DNA.

Preparation of 5'-iodinated Oligodeoxyribonucleotides and 3'-phosphorothioate Oligodeoxyribonucleotides Phosphorylation at the 3' end of DNA strands was carried out with a phosphoramidite reagent (T. Horn et al., Tetrahedron Lett. 27, 4705–4708 (1986)) purchased from Glen Research. Oligodeoxyribonucleotides were synthesized on an Applied Biosystems (ABI) 392 synthesizer using standard β-cyanoethylphosphoramidite chemistry, except that for 3' phosphorothioate sequences, the first nucleotide added after the phosphorylation reagent was sulfurized by the sulfurizing reagent from ABI (H. Vu et al., Tetrahedron Lett. 32, 3005–3008 (1991)). 5' Iodo-oligonucleotides were synthesized as described in Example I.

Ligations to Produce 5'-S-thioester Linkages

Oligonucleotides containing 5'-iodo- and 3'-phosphorothioate groups (20 mM) were incubated with 22 mM complementary splint oligomer in a pH 7.0 buffer (50 mM Tris.borate) containing 10 mM $MgCl_2$ at room temperature for 24 hours as described in Example I. The splint sequence used for the 20mer and 45mer DNAs was

```
5'-d(CTA GTC CAA AGT GCT CGG)    (SEQ ID NO: 4);
``` for the hairpin sequence no splint was needed. Ligation products were isolated by preparative denaturing polyacrylamide gels.

Exonuclease Cleavage

Snake Venom Phosphodiesterase Digestion: 5'-$^{32}$P-labeled oligonucleotides (500,000 CPM), 0.12 mU SVPD (Boehringer Mannheim) were incubated at room temperature in a pH 7.5 buffer (70 mM Tris.borate) containing 10 mM $MgCl_2$, in a total volume of 50 μL. Aliquots (8 μL) were removed at desired time points and stopped by the addition of 8 μL stop solution (30 mM EDTA, 8 M urea).

T4 polymerase digestion: 5'-$^{32}$P-labeled oligonucleotides, 0.2 units T4 DNA Polymerase (United States Biochemical) were incubated at room temperature in a pH 8.8 buffer (33 mM " Tris.HCl) containing 10 mM $MgCl_2$, 66 mM KOAc, 5 mM dithiothreitol, 0.01% bovine serum albumin (BSA), in a total volume of 50 μL. Aliquots (8 μL) were removed at desired time points and stopped by the addition of 8 μL stop solution.

Calf Spleen Phosphodiesterase Digestion: 20mer oligodeoxynucleotides (FIG. 5) were 3' end-labeled with [α-$^{32}$P] ddATP and Terminal Deoxynucleotidyl Transferase (United States Biochemical). They were incubated with 0.2 U CSPD (United States Biochemical) at room temperature in a pH 6.0 buffer (30 mM NaOAc), in a total volume of 30 μL. Aliquots (4 μL) were removed at desired time points and stopped by the addition of 8 μL stop solution.

Endonuclease Cleavage

Endonuclease cleavage: 0.05 nmol dumbbell DNA (FIG. 5) and 50 units NsiI (GIBCO BRL) were incubated at 37° C. for 1.5 h in a pH 8.0 buffer (50 mM Tris.HCl) containing 10 mM $MgCl_2$, 100 mM NaCl, in a total volume of 50 μL. Reactions were stopped by heating at 68° C. for 20 min. After phenol-chloroform extraction and ethanol precipitation, pellets were brought up in 5 μl $H_2O$ prior to loading on an analytical PAGE gel.

Polymerase Studies

Conditions for the primer extension experiment were as follows: 10 nM template DNA strand, 10 nM primer strand (FIG. 5), 1 mM each of dATP, dTTP, dCTP, and dGTP (Boehringer Mannheim), and 3 units Klenow fragment of DNA Polymerase I (exo$^-$, United States Biochemical) were incubated in a pH 7.5 buffer (50 mM Tris.HCl) containing 10 mM $MgCl_2$, 1 mM dithiothreitol, 50 μg/mL BSA) at 37° C., in a total reaction volume of 20 μL. Reactions were stopped by addition of 10 μL stop solution and heated to 90° C. for 2 minutes, followed by chilling on ice prior to loading on the gel.

Conditions for the run-off transcription reactions were as follows: 1 μM template, 50 units T7 RNA Polymerase (New England Biolabs), 0.5 mM each of ATP, GTP and CTP, 60 μM UTP, 0.27 μCi of α-$^{32}$P-UTP were incubated in a pH 7.9 buffer (40 mM Tris.HCl) containing 6 mM $MgCl_2$, 2 mM spermidine, 10 mM dithiothreitol at 37° C., in a total volume of 15 μL. Reactions were stopped by addition of 15 μL stop solution and heated to 90° C. for 2 min, followed by chilling on ice prior to loading on the gel.

Thermal Melting Studies

Solutions for thermal denaturation studies contained a 1:1 ratio of the complementary strands (1.0 μM each). The solution for the 20mer duplexes contained 100 mM NaCl and 10 mM $MgCl_2$ buffered with 10 mM Na.PIPES at pH 7.0. The solutions for the dumbbell duplexes contained 10 mM Na.PIPES at pH 7.0 and 1 mM EDTA. Solutions were heated to 90° C. and allowed to cool slowly to room temperature prior to the melting experiments. Melting studies were carried out in Teflon-stopped 1 cm pathlength quartz cells under a nitrogen atmosphere on a Varian Cary 1 UV-VIS spectrophotometer equipped with a thermoprogrammer. Absorbance was monitored at 260 nm while the temperature was raised from 10° C. to 95° C. at a rate of 0.5° C./min. Melting temperatures were determined by computer fitting using a two-state approximation with linear sloping baselines. Error in $T_m$ is estimated at ±0.5° C. or less.

Results and Discussion

To test the ability of enzymes and varied buffer conditions to cleave P—S bonds in 5' bridging phosphorothioates, a 20mer 5'-S-containing oligonucleotide (FIG. 5) was constructed by ligation of an octamer carrying a 3'-phosphorothioate with a 12mer carrying a 5' iodide in the presence of an 18mer complementary strand. This produces a single sulfur at the 5' carbon of thymidine in the ninth position of this sequence.

Hydrolysis of the P—S bond in the absence of enzymes is expected to be much more rapid than occurs with DNA phosphodiesters, which have a half-life of many thousands of years at neutral pH. To examine this we incubated the 20mer containing a sulfur linkage (FIG. 5) at varied pH (pH 5.0, 7.0, and 9.0) over a four day period. Under these conditions no specific cleavage is visible (<1%) at any pH. This allows us to set an upper limit for the hydrolysis rate constant for this P—S bond at $k_{obs}=3\times10^{-8}$ sec$^{-1}$ or less, and the half-life of the bond is therefore greater than one year at pH values near neutral. The corresponding half-life for 5'-bridging thioesters in RNA is three days (H. van Tol, et al., Nucleic Acids Res. 18, 1971–1975 (1990)). It is worth noting that such linkages in DNA can be cleaved rapidly, if desired, in the presence of silver nitrate (M. Mag et al., Nucleic Acids Res. 19, 1437–1441 (1991)).

We then investigated the susceptibility of this linkage ([5'-$^{32}$P]dGATCAGGTp$_s$TTCACGAGCCTG    (SEQ ID NO: 5), where "s" denotes position of sulfur in phosphorothioate linkage) to different exonuclease enzymes, specifically, the 3'-exonuclease activity of T4 DNA polymerase, snake venom phosphodiesterase (SVPDE) (a different 3' exonuclease), and calf spleen phosphodiesterase (CSPDE), which is a 5'-exonuclease. We found that sulfur causes a significant inhibition of T4 exonuclease activity. The pauses occur at sites one and two nucleotides 3' (prior) to the thioester rather than during the removal of the sulfur-containing nucleotide itself. We estimate the cleavage of the most resistant linkage to be inhibited by a factor of five to tenfold. Since the S—P bond is not expected to be cleaved by this enzyme (products with this enzyme are normally 5'-monophosphates), we surmise that this pause is due to unfavorable interaction of the enzyme with this sulfur, possibly because of the increased bond lengths or relatively poor hydrogen bond accepting ability of the sulfur relative to oxygen.

Interestingly, the snake venom 3' exonuclease showed no visible inhibition by the presence of a bridging sulfur. This enzyme also produces 5' phosphates and would not be expected to break the P—S bond in the thioester. It is clear that the interactions of this enzyme with DNA are significantly different than those in the exonuclease domain of T4 polymerase, or that the bond length sensitivity is much lower for the snake venom enzyme. It is worth noting that the only previous report of SVPDE cleavage by 5'-bridging sulfur linkages in DNA reported significant slowing of the enzyme (V. Rybakov et al., Nucleic Acids Res. 9, 189–201 (1981)). However, in that case all linkages were modified rather than a single one as in the present case, a fact which might explain the differences.

The final enzyme, calf spleen phosphodiesterase, which is a 5' exonuclease that produces 3' phosphate products, was studied for its ability to digest a 21mer with sulfur between the 8th and 9th nucleotides. This case is particularly noteworthy since this enzyme would be expected to cleave the P—S bond in the 5' bridging sulfur linkage. In this experiment a significant pause was observed, although cleavage beyond this point clearly does occur, eventually yielding only very short products. The pause occurs at the position assigned to the nucleotide immediately before the linkage, which indicates that cleavage of the P—S bond by the enzyme is slower than processing of a normal P—O bond. Since sulfur is expected to be a much better leaving group than oxygen in the absence of an enzyme, we surmise that this inhibition arises from less favorable protein (or protein-bound metal) electrophilic interactions with the leaving group. Alternatively, it is possible that the increased bond lengths cause a geometric problem at the active site. The P—S bond and the S—C bond in the diester linkage are each expected to be approximately 0.4 Å longer than the analogous P—O and O—C bonds in unmodified DNA (W. Knight et al., Biochemistry 30, 4970–4977 (1991)).

Figure 6:
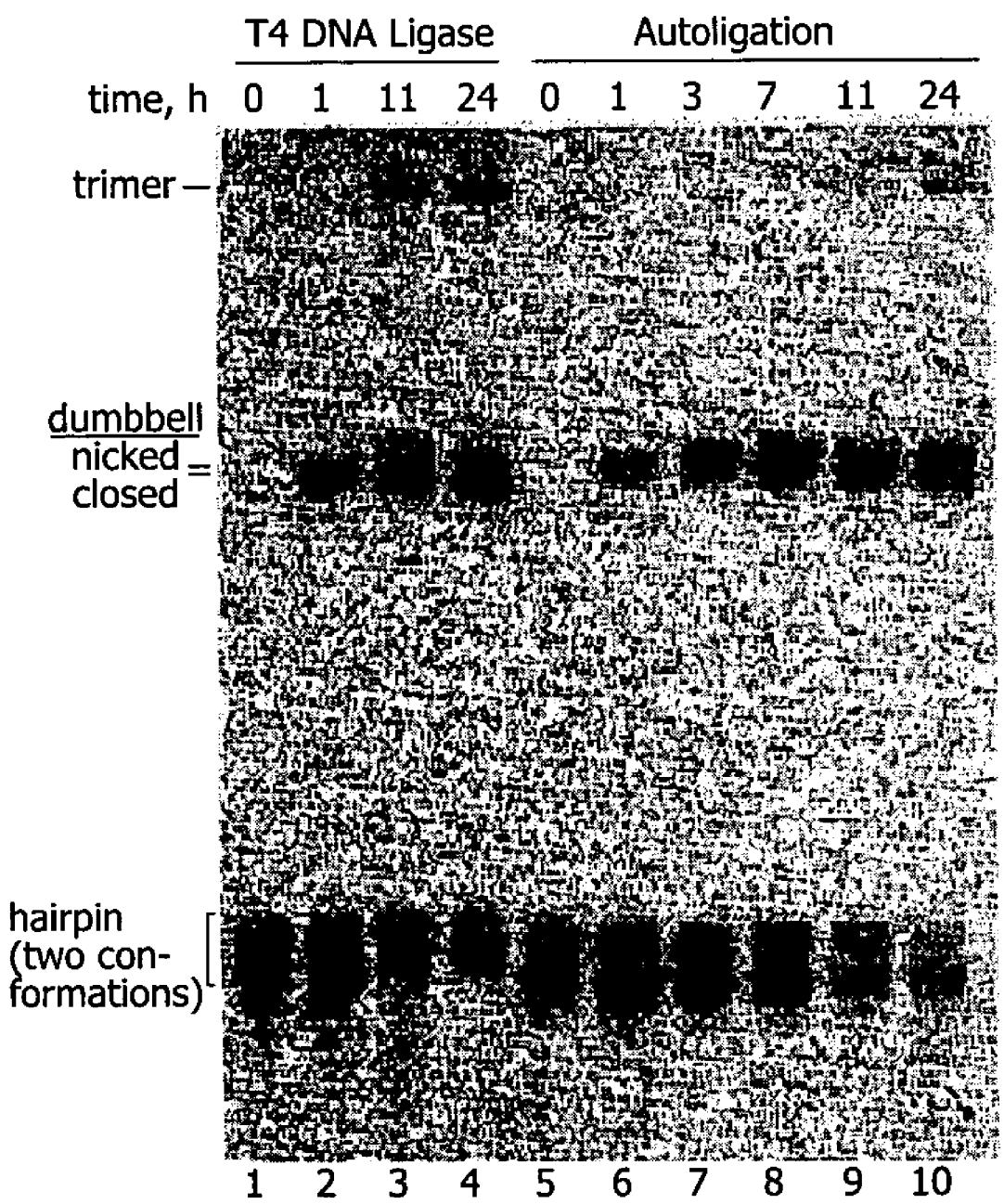
FIG. 6 shows the time course of autoligation of a hairpin DNA to closed circular dumbbell form at 25° C. (lanes 5–10), with comparison to ligation mediated by T4 DNA ligase in the same sequence (lanes 1–4); complete reaction requires two ligations, the first of which joins two hairpins (creating a nicked dumbbell), and then a second, which closes the dumbbell into circular form; the sequence of the autoligating hairpin is 5'-I- d(TCCAGCGTACTTTTGTACGCTGGATGCA)-$p_s$-3'    (SEQ ID NO: 1), and that of the comparison hairpin is d(pTCCAGCGTACTTTTGTACGCTGGATGCA) (SEQ ID NO: 2).

We then tested the ability of a site-specific endonuclease to cleave a double-stranded sequence containing the 5'-bridging sulfur. For this study a hairpin-forming sequence with a self-complementary overhang was ligated with another copy to produce a dumbbell DNA consisting of a 24 bp duplex capped by 4 nt loops (FIGS. 5 and 6). The two sulfur linkages are present at the cleavage site of restriction endonuclease NsiI in its 6 bp palindromic recognition sequence. An unmodified version of this sequence was constructed as a control. Although the unmodified sequence is completely cleaved by the enzyme in 1.5 hour, the sulfur-containing sequence shows no cleavage over this period. The enzyme would not be expected to cleave the P—S bond since it normally leaves 5' phosphate ends. This inhibition must therefore be due to unfavorable interactions between the enzyme and the 5'-bridging position, or to altered geometry of the DNA arising from the longer P—S bonds.

We also investigated the question of whether the increased bond lengths (S—C and S—P) in the modified DNA would be recognized as a template for common polymerase enzymes. This question has not previously been examined with this class of linkage. For this we constructed a 45mer template with sulfur after the 37th position from the 3' end. Thus, binding of a 17mer primer at the 3' end allows DNA polymerase extension for 20 nucleotides up to the sulfur position. This primer also acts as a promoter top strand for T7 RNA polymerase, thus allowing both DNA and RNA polymerase to be tested on the same template. Once again, an unmodified template was tested for comparison. The polymerases studied were the Klenow fragment (Kf) of E. coli DNA polymerase I (exo-mutant) and T7 RNA polymerase.

Interestingly, both the DNA and RNA polymerases proceeded beyond the sulfur-containing thymidines with no apparent pause seen before, at, or after this residue. No difference is observed in the length of the products or in the amount of time necessary to reach this full length with these concentrations of enzyme and DNA. Thus these polymerases apparently recognize no difference between the oxygen and sulfur-containing templates under these conditions, despite the longer bonds in the latter case.

Finally, we examined the effects of one or two 5' bridging sulfur linkages on the thermal stability of DNA—DNA duplexes. This was tested first in the context of a 20mer duplex carrying one sulfur linkage in one strand (d(GAT CAG GTp$_s$T TCA CGA GCC TG))   (SEQ ID NO: 6)

and its unmodified 20mer complement), and a completely unmodified duplex of the same sequence was examined for comparison. Thermal denaturation studies (100 mM Na$^+$, 10 mM Mg$^{2+}$) showed that both cases were well-behaved, showing sharp transitions. $T_m$ values were 68.8° C. for the sulfur-containing duplex and 71.5° C. for the unmodified duplex. A second case was then examined with 5'-S linkages in both strands of a duplex, this time using the dumbbell sequences shown in FIG. 7). Because of their high stability the denaturation studies were performed under low salt conditions (10 mM Na.PIPES, 1 mM EDTA). The results showed that the thermal stabilities of the modified duplex ($T_m$=82.8° C.) and the unmodified one ($T_m$=83.3° C.) are essentially the same. Thus, the 5'-bridging sulfur linkage causes very little destabilization of duplexes, at least for the cases studied here.

The results show overall that the 5' bridging sulfur causes significant inhibition of some nuclease enzymes but no apparent inhibition of DNA or RNA polymerase enzymes. In terms of stability in the absence of enzymes, the 5'-thioester linkage is likely to be considerably more labile to hydrolysis than natural DNA phosphodiesters, but is stable at least for months at pH values of 5 to 9. This linkage is much more stable, therefore, than previously reported 5' bridging thioesters in RNA. However, when specific cleavage is desired in thioester-linked DNA, treatment with silver produces cleavage under mild conditions (M. Mag et al., Nucleic Acids Res. 19, 1437–1441 (1991).

Example III

High Sequence Fidelity in a Nonenzymatic DNA Autoligation Reaction

Introduction

The ability to detect single base differences in DNA is of great importance in molecular genetics. Specific identification of point mutations is playing an increasingly important role in diagnosis of hereditary disease and in identification of mutations within oncogenes, tumor suppressors genes and of mutations associated with drug resistance. Oligonucleotides can distinguish single nucleotide differences by small changes in hybridization efficiency, however the selectivity seen for oligonucleotide probes of 20 nt or longer is relatively small.

One of the most common strategies in current use for engendering high specificity in sequence detection is the use of DNA ligase enzymes. Ligases such as the T4 and Tth enzymes are quite sensitive to base mismatches at the ligation junction, and thus these enzymes are used as the basis for methods such as ligase chain reaction (LCR) and ligase detection reaction (LDR). Enzymatic ligation selectivities against single base mismatches are high, on the order of 10 to 100-fold for T4 DNA ligase, and 100–10,000-fold for the Tth enzyme.

Non-enzymatic (chemical) methods for ligation may have some possible advantages over ligase enzymes in application to detection of mutations. Among these are lower sensitivity to nonnatural DNA analog structures, the ability to be ligated on RNA targets, lower cost, and greater robustness under varied conditions. In addition, non-enzymatic ligations might possibly be carried out inside intact cells or tissues which might not be accessible to ligase enzymes added to the medium.

Oligonucleotides formed by the reaction of phosphorothioates at the 3' end of one strand with a leaving group (such as tosylate or iodide) on thymidine in the adjacent strand (Example I) differ from natural DNAs only by replacement of a single oxygen atom with sulfur. Because of the close resemblance to natural DNA, the junction apparently does not affect the ability of polymerases to replicate or transcribe the sequence (Example II), which makes this ligation approach particularly promising for sequence detection methods that require further manipulation such as DNA amplification. This Example reports studies delineating the sensitivity of the phosphorothioate-iodide DNA autoligation reaction to single nucleotide mismatches at or near the ligation junction. This is investigated in the context of H-ras target sequences both with dual probes ligating on the single-stranded target DNA as well as for single probes designed to self-ligate intramolecularly to circular form ("padlock" probes (M. Nilsson et al., Science, 265, 2085–2088 (1994)). The data show that optimized placement of a single-base mismatch can lead to selectivities comparable to those seen with ligase enzymes.

Preparation of Autoligation Probes

All oligodeoxynucleotides were synthesized on 1 μmole scale on an ABI model 392 synthesizer using standard β-cyanoethylphosphoramidite coupling chemistry. The 3' end phosphorothioate groups required for the ligation reaction were incorporated into DNA strands substantially as described in Examples I and II. Briefly, the oligonucleotide synthesis was carried out with a 3' phosphate controlled pore glass support (Cruachem). The first nucleotide unit was added with normal oxidation being replaced by a sulfurizing reagent (Applied Biosystems). The remaining synthesis and deprotection were as for the standard DNA cycle. The second requirement for ligation is a 5' end carrying an iodide. This is added with a commercially available 5-iodothymidine phosphoramidite reagent (Glen Research). Deprotection and removal of iodine-containing strands from the CPG support was done by incubation in concentrated ammonia for 24 hours at 23° C. to avoid small amounts of degradation which occur at 50° C. Probe DNAs were then lyophilized and used without further purification, to avoid disulfide formation of the phosphorothioate ends. Analytical gels showed the purity of phosphorothioate and iodide probes to be better than 90%.

Purification of target oligodeoxynucleotides was carried out by preparative denaturing polyacrylamide gel electrophoresis. All DNAs were quantitated by UV absorbance using the nearest neighbor approximation to calculate molar absorptivities.

Ligation Reactions

Reactions were performed in 600 μl pH 7.0 Tris-borate buffer containing 10 mM MgCl$_2$, with target and probe DNA concentrations of 1.3 or 20 μM. Ligations with radiolabeled probes also contained 50 μM dithiothreitol. Reactions were incubated at the indicated temperatures. Aliquots (100 μL) were removed at various times and then were frozen and lyophilized for one hour. Pellets were taken up in 5 μl water-formamide-urea loading buffer. Samples were heated to 95° C. for 2 minutes and then chilled on ice prior to loading on a 20% polyacrylamide gel containing 8 M urea. Gels were visualized with Stains-All dye (Sigma) and quantified by densitometry using NIH Image version 1.62b7 software. For radiolabeled probes, radioactivity was quantitated on a Molecular Dynamics Phosphorimager. The circular identity of the intramolecular probe after ligation was confirmed by isolation and treatment with S1 Nuclease. This produced a second major band which co-migrated with the linear precursor.

Intermolecular Autoligation

To evaluate the effects of complementary and mismatched template DNAs on the phosphorothioate-iodide autoligation reaction, we synthesized two probes ten and seven nucleotides in length carrying a 3'-phosphorothioate and a 5'-iodothymidine, respectively. The sequences are given in FIG. 8. We also synthesized four 28mer target DNAs which correspond to the fully complementary sequence (MUT) and singly mismatched targets where the position of the mismatch is at the 3' and 5' side of the junction (templates 3'MM and 5'MM, with G-A and T-C mismatches respectively), and one in which a G—G mismatch is centered on the 7mer iodo-probe (template MMM ("mid-mismatch")). The sequence of the fully complementary target corresponds to that of the codon 12 mutation commonly found in the H-ras oncogene, while the 3'MM target corresponds to the unmutated protooncogene sequence.

Ligations were carried out at pH 7.0 in a buffer containing 10 mM $Mg^{2+}$. We tested the effects of probe+target concentration and temperature on the extent and rate of ligation. The products of ligation were analyzed by following time courses over 24 hours, and were examined by denaturing gel electrophoresis. Yields as a function of reaction time were quantitated by densitometry.

Simple qualitative inspection of gels for a given set of reactions with these linear probes showed that both the reaction conditions and the relative placement of the mismatch are significant factors affecting the ligation yield. At 37° C. and 1.3 µM probe and target concentration, the ligation proceeded to high conversion over 9–18 hours with the complementary target, while only very little product was observed in the 3'MM and 5'MM cases, and none at all in the MMM case. We also examined the same sets of ligations at 20° C. with 1.3 µM DNA and at 37° C. with 20 µM DNA, and the results were qualitatively similar.

Quantitative comparisons of these three sets of conditions indicate that selectivity was highest at 37° C. with 1.3 µM target and probe concentrations (FIG. 9). In all three cases, the mid-mismatch (MMM) gave the highest level of discrimination; there was little difference between the junction mismatches (3'MM and 5'MM), which overall gave lower levels of discrimination. At the two sets of conditions having lower DNA concentration there was no observable ligation on the MMM template at 24 hours; we estimate that the densitometry could have detected 4% or higher yield at the last time point. This suggests selectivity of greater than one order of magnitude (see below). In some of the slow ligation cases, a leveling off of the reaction appeared to occur. In these cases it is possible that there was a small amount of disulfide formation between phosphorothioate probes that makes the kinetics appear biphasic. We have observed DTT-sensitive slower-moving dimer bands when the probes are at high concentrations (such as during precipitation). The quantitative kinetics experiments with radiolabeled probes were carried out with DTT present (below) to avoid possible disulfide formation.

Intramolecular Autoligation/Cyclization

We then investigated whether such ligations could be carried out intramolecularly to yield circular products. This type of ligation would be the nonenzymatic equivalent of those carried out with "padlock"-type probes. Initially, the probe DNA was designed to form 10 base pairs on either side of the junction; the sequences are shown in FIG. 8. The reactions were again observed qualitatively, with analysis after 24 hours, and quantitatively, by following a time course under varied conditions (FIG. 10). Since the reaction is intramolecular we varied 25 temperature (37° C. and 70° C.) but not concentration.

The results showed that the intramolecular phosphorothioate-iodide ligation proceeded in high yields with a fully complementary (MUT) target, and that there was significant selectivity against single mismatches. In contrast to the intermolecular ligation, however, the levels of discrimination appeared to be somewhat lower. For the mismatches, the most ligation was seen with the central mismatch (MMM), which showed 2-fold discrimination in yield at 24 hour. Somewhat greater selectivity occurred with the 3' and 5' junction mismatches (3.5- and 2.5-fold). This is the reverse of what was observed for ligation of the intermolecular 7mer+10mer probes, which showed highest discrimination in the MMM case. At 25° C. with the cyclization probe, the MMM case showed only a very small amount of discrimination relative to the fully complementary sequence, while at 70° C. the MMM discrimination increased somewhat (FIG. 10(a)). The magnitude of selectivity at 70° C. in the "padlock"-type case was similar to that seen for the 3'MM and 5'MM cases for the intermolecular reaction.

Figure 11A:
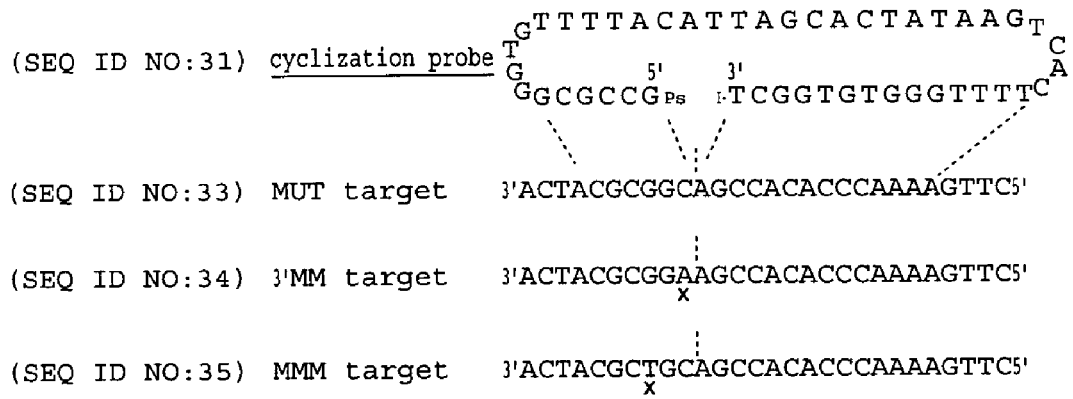
Figure 11B:
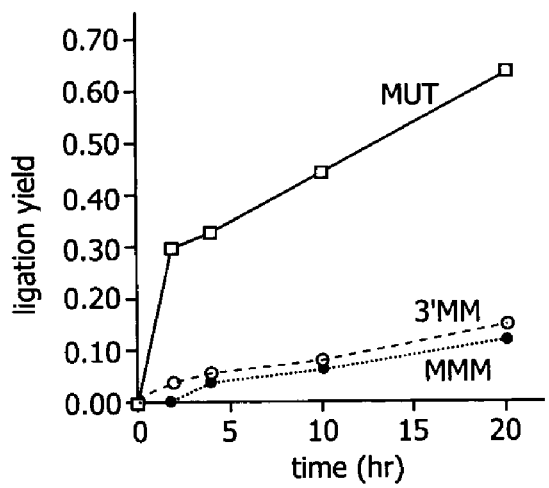

To test whether this ligation would be more sensitive to mismatches when located in a shorter binding domain, three new target DNAs were constructed (FIG. 11(a)). Binding of the cyclization probe to these new targets would give hybridization that still totals 20 base pairs, but arranged with 6 bp on one side of the junction and 14 bp on the other side. The MMM case had a mismatch that fell within the shorter 6 bp binding domain. Ligation experiments were again carried out with the three targets at 70° C. The data (FIG. 11(b)) showed that with this new sequence, selectivity against a mismatch at the junction was similar to that seen with 10 bp+10 bp of hybridization. However, when the mismatch fell within the shorter binding domain, the selectivity was increased. At 20 hour the comparative yields for the 6 bp+14 bp case were 65% for the complementary (MUT) template and 13% for the mismatched (MMM) one. This compares favorably to the 10 bp+10 bp case, which displayed yields of 63% (MUT) and 32% (MMM) at 24 hour. It should be noted that the sequences were different in the 10+10 and 6+14 cases, however.

Optimized Ligation of Two Probes for H-ras

The results indicated that in the intermolecular ligation, highest levels of discrimination would be observed with a mismatch located centrally in a short 7mer probe. To attempt to apply this optimized strategy to detection of the ras codon 12 mutation, we constructed two new probes (FIG. 12 (a)) in which the well-characterized G->T transversion (C->A in the complementary strand) could be targeted with the best mismatch location. We then evaluated the relative rates of ligation as described above, using the MUT 50mer complementary target (corresponding to the mutated oncogene) and the WT 50mer target (corresponding to the wild-type sequence). In this case the expected mismatch is a T-C located at the center of the 7mer phosphorothioate probe binding site.

The ligation was carried out at 37° C. with 1.3 µM DNA and probes, conditions under which the earlier set of probes gave highest discrimination. The shorter phosphorothioate probe was 5' radiolabeled to obtain greater sensitivity for quantitative rate measurements. The results are plotted as a time course in FIG. 12(b), which shows a quite large difference for the two targets. The data for the complementary ligation (MUT template) could be fit well using a second-order kinetic fit giving a rate constant of 29.1 $M^{-1}sec^{-1}$. The initial rates were measured for the two templates (FIG. 12(c)), and this allowed us to determine a rate constant of 0.16 $M_{-1}sec^{-1}$ for the same probes with the mismatched (WT) template. Thus, the rates are different by a factor of $1.8\times10^2$-fold, a level of discrimination comparable to that seen for ligase enzymes (see below).

Ligation Selectivity

Because the ligation experiments in this Example were aimed primarily at quantitating and optimizing fidelity of the reaction, only single-stranded targets were used. However, it is fully expected that more complex double-stranded DNA sequences can also be used as a target.

A number of viable strategies for overcoming problems presented by hybridization to double-stranded targets have been noted in studies of other sequence detection methods, and a have been described (U. Landegren et al., Science, 241, 1077–1080 (1988); H. Gamper et al., J. Mol. Biol., 197, 349–362 (1987); V. Somers et al., Biochim. Biophys. Acta, 1379, 42–52 (1998)), and our preliminary studies have shown success with relatively long double-stranded sequences in slot-blot assays (see Example II).

The present results show that the phosphorothioate-iodide autoligation reaction can proceed with good yields and high selectivities against single base mismatches, particularly when the mismatch falls near the center of a heptamer probe. In the optimized cases, G—G or C-T mismatches are selected against by a factor of at least two orders of magnitude. This level of specificity is higher than that seen for the same mismatches using phage T4 DNA ligase or *Chlorella* virus DNA ligase, although it is not as high as that seen for the more discriminating bacterial Tth ligase under optimized conditions. Application of this autoligation to current assay methods such as LDA (ligase detection assay) and ligation-mediated PCR is also envisioned.

It is of interest to consider the physicochemical origins of the selectivity for this autoligation reaction. The data show that selectivity is lower at the ligation junctions but higher near the center of a short probe. We surmise, therefore, that the chief factor in successful ligation is the binding affinity of the probe rather than the precise geometry at the ligation junction. This is consistent with our finding that the reaction proceeds with second-order kinetics. In contrast, enzymatic ligations are commonly most selective at the junction, a fact which is attributed to the precise geometric control that the enzyme takes in orienting the reactive groups for in-line attack at phosphorus (N. Higgins et al., Meth. Enzymol., 68, 50–71 (1979)). For the present reaction it seems that the transition state $S_N2$ geometry can be reached even with mismatched geometries; this is likely due to the relatively high flexibility of the DNA at the nicked junction. Presumably, ligase enzymes curtail this mobility to a high degree.

It should be noted that in the present Example, since the iodide exists only on a thymidine residue, there is a sequence limitation in which an adenine must be present at the desired ligation site. If either sense or antisense strands of the DNA target can be probed, then the restriction is relaxed to either T or A at the junction, which means that at least half of all possible sites can be probed optimally. In most applications the ligation junction can be shifted by one or two nucleotides as needed, therefore this is not expected to be a major problem. Indeed, since there is likely to be at least ±1 nt of latitude injunction placement for a given point mutation, and since the ligation junction can be placed either 5' or 3' to the mutation, the restriction is calculated to be a significant hindrance in only about 5% of possible sequences. Nevertheless, there is a simple answer to this problem: an iododeoxycytidine nucleoside variant of the 5'-iodoT used here could be utilized. While not commercially available at present, we anticipate that it could be readily produced.

Advantages of Autoligation Over Enzymatic Approaches

There are a number of aspects of the autoligation reaction which may give it advantages over standard enzymatic approaches. Since no enzymes or added reagents are needed, the ligation might be carried out in media that would prevent enzymatic reactions. For example, it is conceivable that the ligation could be carried out inside whole cells or tissue samples, or in gels, solvents, or physical conditions not amenable to enzyme permeability or stability. The ligation proceeds well in the presence of millimolar amounts of dithiothreitol, thus it is feasible that the reducing environment of the cell might not interfere with reactivity. Another benefit of the autoligation is that it can be used with short probes such as heptamers, which cannot be ligated by the commonly used Tth ligase. In addition, the absence of enzyme requirements makes it feasible to carry out ligations of structures which are not substrates for DNA ligases. Examples of this might be the ligation of DNA probes on RNA targets, and the use of chemically modified DNA probes. A further benefit of this autoligation reaction relative to enzymatic methods is that the 3' probe cannot serve as a primer for polymerases, since it has a phosphorothioate group blocking the 3' hydroxyl. In standard enzymatically ligated probes, both unligated probes as well as the product can potentially act as primers. It is worth pointing out that since the phosphorothioate and iodide probes are constructed on an automated synthesizer using commercially available reagents, requiring no post-synthesis modification, these potential benefits can be realized without any additional preparative effort over standard methods.

Example IV

Nonenzymatic Autoligation in Direct Three Color Detection of RNA and DNA Point Mutations Summary The use of nonenzymatic phosphorothioate/iodide DNA autoligation chemistry for the detection and identification of both RNA and DNA sequences is described in this Example. Combining ligation specificity with the hybridization specificity of the ligated product allowed discrimination of a point mutation of as high as >104-fold. Unlike enzymatic ligations, this self-ligation reaction was found to be equally efficient on RNA or DNA templates. The reaction was also found to exhibit a significant level of self-amplification, with the template acting in catalytic fashion to ligate multiple pairs of probes. The autoligating energy transfer (ALET) probe design offers direct RNA detection combining high sequence specificity with an easily detectable color change by fluorescence resonance energy transfer.

Preparation of Probes and Targets

The goals of the work reported in this Example were to investigate the scope of this autoligation chemistry on varied sequences with RNA or DNA substrates, and to test methods for detecting the products of ligation. To carry this out we chose a probe design involving ligation of 7mer and 13mer probes (FIG. 13), which can afford very high sequence specificity due to the high mismatch selectivity of the shorter of these probes. We utilized probes complementary to the H-ras protooncogene and to the well-characterized codon 12 G->T mutation. Two 7mer probes (mutant and wild-type) were designed such that the position of the point mutation fell at the center position, to maximize selectivity, and were constructed with 3'-end phosphorothioate groups to act as nucleophiles in the ligation. Coupled with these mutation probes was a 13mer probe designed to bind directly adjacent to the mutation probes. This longer "universal" probe was expected to bind equally strongly to wild-type as well as mutant targets. Studies were initially carried out with a single pair of probes at a time (one radiolabeled 7mer and the 13mer), and later studies were carried out with the three probes simultaneously, each carrying a different fluorescent label.

Specifically, DNA and RNA oligonucleotides were synthesized on 1 μmol scale on a Perkin Elmer/Applied Biosystems 392 synthesizer using standard β-cyanoethylphosphoramidite coupling chemistry. Phosphorylation was carried out using Phosphate-on reagent from Glen Research. For 3'-phosphorothioate sequences, the first nucleotide added after the phosphorylation reagent was sulfurized by the sulfurizing reagent from ABI. 5'-Iodo-oligonucleotides were synthesized by published procedures using iodo-T phosphoramidite from Glen Research, as described in Examples I and II. Automated RNA synthesis was carried out using t-butyldimethylsilyl-protected phosphoramidites from Glen Research. Oligonucleotides were deprotected in 3:1 concentrated ammonia: ethanol at 55° C. for 18 hours and dried. Silyl protecting groups were removed by adding 400 μL 1M tetrabutylammonium fluoride in tetrahydrofuran (Sigma) to the residue and shaking at room temperature for 24 hours. RNA was desalted on a Sep-pak column (Water) and purified by denaturing polyacrylamide gel electrophoresis.

FAM and HEX labels were introduced with FAM-thymidine and 5' HEX phosphoramidites (Glen Research), during automated DNA synthesis. Labeling of ROX was done by conjugation of the NHS ester with 5' amino modified DNA. The 5'-amino-modifier C6 (Glen Research) was introduced into the 5' end of the probe during automated DNA synthesis. The MMT protecting group was removed by detritylation for 5 minutes right before the dye labeling reactions. To prevent the potential reaction of the 3' phosphorothioate with the NHS ester of the dye, the labeling reaction was carried out before DNA was cleaved from the beads. 2 mg of 6-carboxy-X-rhodamine succinimidyl ester (Molecular Probes) was dissolved in 200 μL of dimethylformamide immediately before reaction. The reaction solution was prepared by adding 400 μL 0.5 M sodium bicarbonate (pH 7.6) and 400 μL water to the above dye DMF solution. DNA on the silica was added to the mix and allowed to react at room temperature for 1 hour with slow shaking (vigorous shaking is to be avoided). DNA beads were recovered by filtering the reaction mixture through glass wool and rinsed with water and acetonitrile several times.

All dye-labeled oligonucleotides were cleaved and deprotected in ammonium hydroxide at room temperature for 24 hours, and lyophilized. They were quantitated without further purification using nearest neighbor methods, subtracting the dye's contribution at 260 nm. The degrees of substitution of all three probes were determined to be above 90%.

Plasmid pT24-C3 containing the c-Ha-ras 1 activated oncogene mutation at codon 12 (GGC-GTC) and pbc-N1, containing wild type c-Ha-ras were obtained from American Type Culture Collection. 300 bp regions including nucleotides −53 (relative to the transcription initiation site) and +244, of normal and activated Ha-ras genomic clones were PCR amplified using the primers 5'-GTG-GGG-CAG-GAG-ACC-CTG-TA(SEQ ID NO:7) (sense) and 5'-CCC-TCC-TCT-AGA-GGA-AGC-AG(SEQ ID NO:8) (antisense).

Steady State Fluorescence

Measurements were performed on a Spex Fluorolog-2 fluorimeter using a bandwidth of 1.8 nm and 1×1 cm quartz cuvettes. The source of radiation was a xenon arc lamp. All slits were set to 2 mm, resulting in approximately 3.4 nm resolution. Fluorescence measurements were taken in the right angle mode. Emission spectra were corrected for instrument response. FRET spectra were measured at FAM's excitation wavelength which is 495 nm.

Ligation Reactions on DNA and RNA Templates

To investigate the rate of the 7mer plus 13mer ligation reaction, and to test whether RNA as well as DNA targets would support the reaction, we prepared synthetic 40mer targets of DNA and RNA having the same H-ras mutant target sequence. Ligations were carried out at 25° C. at 1 μM probe and target concentrations, in a pH 7.0 Tris buffer containing 10 mM $Mg^{2+}$ ($MgCl_2$). A time course of the reaction was followed using 20% denaturing polyacrylamide gel electrophoresis of reactants and products. Fluorescent bands were visualized over a UV transilluminator and images were recorded using a Kodak DC120 digital camera.

Results showed that the reaction takes place over a period of hours on the DNA template (FIG. 14), reaching the 50% stage in approximately 6 hours. Significantly, the reaction on the RNA template is observed to occur at virtually the same rate as on the DNA.

Turnover Experiments

DNA templates have in some cases been observed to foster the ligation of multiple equivalents of ligating strands, by dissociation of the ligated product followed by binding and ligation of a new pair of ligating strands. This turnover is commonly inhibited by the stronger binding of the product than the unligated strands to the template, but if it occurred even to a relatively small degree, it would be valuable to possible diagnostic applications, since one target would engender more than one ligated signal. The present phosphorothioate-iodide ligation results in a duplex weakly destabilized relative to natural DNA (see Example II) and so might be expected to give some degree of turnover, but with significant product inhibition. Nonetheless, we investigated whether a degree of amplification might be possible in this reaction.

We therefore investigated the yields of ligated product as a function of target concentration, from 1–100 nM, and temperature. Experiments were carried out on a synthetic MUT DNA target using FAM labeled probes. Specifically, 100–10,000 equivalents of probes per equivalent of DNA target strand were present with target concentration from 1–100 nM. Reactions were carried out at 25° C., 37° C., 50° C. or with thermal cycling for 24 hours, and were then analyzed by denaturing gel electrophoresis. Images were obtained by FluorImager and quantitated by ImageQuant (Molecular Dynamics).

Figures 15A, 15B:
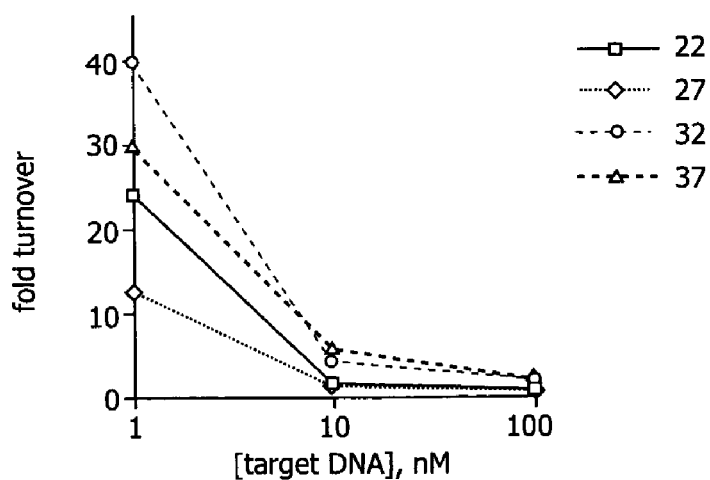

Results are given in FIG. 15(a) and compared graphically in FIG. 15(b). The results showed that there is significant turnover of autoligation observed at the lower target concentrations. The most efficient conversion is seen with the 32° C. incubation, under which the binding equilibrium and $S_N2$ displacement reaction rate may be best balanced. At the lowest target concentration we observe 40 turnovers (producing 280 fmol of ligated signal for 7 fmol of target). In general, cycling is found to increase turnover only by a small amount (by up to 1.5-fold).

Slot-Blot Analysis

To examine whether the autoligation chemistry would proceed on DNAs affixed to nylon membranes, we obtained plasmids encoding wild-type H-ras and the codon 12 G->T point mutation. Their sequences were independently confirmed by automated Sanger sequencing. We prepared two 300 bp duplexes corresponding to these two sequences by polymerase chain reaction, and affixed them to nylon membranes in the slot blot format. Specifically, crude PCR products were denatured and adsorbed onto positively charged Zeta-Probe nylon membrane using a slot-blot manifold (Bio-Rad) according to manufacturer's instructions. Membranes were incubated for 1 hour at 37° C. in 6×SSC prehybridization solution containing 5× Denhardt's solution (0.1% w/v polyvinylpyrrolidone, 0.1% w/v Ficoll type 400, 0.1% w/v BSA), 100 ug/ml salmon sperm DNA, 0.05% (w/v) sodium pyrophosphate, and 0.5% (w/v) SDA. After prehybridization, membranes were incubated at 37° C. for 18 hour in 6×SSC hybridization solution containing 0.05% sodium pyrophosphate, 0.13 µM of probe UNIV, 0.01 µM of 5'-$^{32}$P-labeled MUT and 1 mM dithiothreitol. The specific activity of the probe was ca. 0.5 µCi pmol$^{-1}$. The membrane was rinsed once in 6×SSC for 15 minutes at room temperature. Exposure to x-ray film was carried out at −70° C. with two intensifying screens. Subsequent washes, when used with preligated 20mer probes, was carried out with 2×SSC at 60° C. for 30 minutes each time.

These experiments showed that the extent of ligation reached a maximum after about 10 hours, and that a strong signal was observed with the complementary mutant DNA (FIG. 16). No signal was observed with radiolabeled 7mer alone or with probes lacking sulfur, confirming that ligation was necessary for producing this signal. Importantly, very little signal was observable under the same conditions with wild-type H-ras DNA differing by a single base; quantitation showed a difference of 788-fold in signal for the two closely related targets.

In such a ligation reaction, there are two possible sources of specificity: the ligation reaction itself, and the hybridization selectivity of the ligated product. In the above experiment it was possible that the ligation occurred indiscriminately, and that the complementary ligated 20mer was remaining bound only to its complementary target. To investigate this possibility we constructed a pre-ligated 20mer probe and labeled it in identical fashion. It was then hybridized to the two DNAs in the slot-blot apparatus under the same conditions as the ligating probes. Results showed that this 20mer hybridized almost equally well (1.8:1) to complementary and mismatched targets under these hybridization and low stringency single wash conditions, giving equal signals for matched versus mismatched DNA. Thus, almost all the selectivity observed above was a result of the ligation reaction alone. However, under increasing stringency of washing, the ligated 20mer does shows significant hybridization selectivity (FIG. 16 (b)); after the 8th wash at 60° C. with 2×SSC we measured a 180:1 ratio of correct to mismatched signals. The total selectivity achievable by the autoligating probes is the product of the ligation and hybridization selectivities, which here is measured to be between 10$^4$ and 10$^5$. Thus, a false positive signal is much lower than the correct signal with equal amounts of DNA, suggesting that such probes could potentially discriminate this mutation in the presence of a 10$^4$-fold or greater excess of wild-type DNA. Subsequent experiments, described below, showed that specificity could be further increased by direct competition of the short probes.

Energy Transfer Probe Design

Fluorescence is a convenient signal for solution-based diagnostic methods, and energy transfer can be used to report on the proximity of two molecules or groups. We therefore investigated whether FRET could be coupled to the autoligation reaction to give a detectable signal that responds only when the bond is formed. Simple side-by-side binding of two appropriately labeled oligonucleotides on a DNA target is known to result in energy transfer. In the present case we did not wish for such a signal to be observable until actual ligation occurred, since the ligation adds a high degree of sequence specificity. We felt it possible that the use of one very short probe might prevent simple binding-induced FRET because it might not saturate the binding site adjacent to the longer probe. If binding-induced FRET could be prevented, it would not be necessary to dissociate the ligation product from the polynucleotide template before assessing whether FRET has occurred. Thus, our design (FIG. 17) included the use of a 13mer universal probe labeled with the FRET donor 5-carboxyfluorescein (FAM) and a 7mer mutant probe 5'-end-labeled with the acceptor dye rhodamine (ROX). Excitation of the FAM dye in unligated probes should lead almost exclusively to green FAM emission (520 nm); however, after ligation the resulting energy transfer might be expected to result in ROX emission (602 nm) coupled with quenching of FAM emission. With these probe sequences there is a thymidine in the universal probe ten nucleotides from the position of the ROX label. We chose this as the site for FAM labeling, since suitably labeled deoxyuridine is readily available, and since this distance is near the optimum for energy transfer.

In this dual probe strategy, one expects to see a color change on detection of H-ras codon 12 mutations, but no change in the presence of H-ras wild type DNA. Since such a negative signal might be confused with false negatives (such as when no DNA is present or no ligation occurs), we sought to include a different color change for detection of wild type DNA. To do this we prepared a third (WT) probe carrying a different FRET acceptor dye, hexachlorofluorescein (HEX) (FIG. 17). If this were ligated to the FAM-labeled universal probe, energy transfer would result in a color change from green to yellow, corresponding to HEX dye emission (556 nm). Simultaneous use of all three probes might be possible, wherein the two short probes carrying acceptor dyes compete for ligation to the universal probe. In principle, a yellow signal would represent detection of wild type target, a red signal would represent mutant target, a combination of the two would represent a mixture, and a green signal would indicate absence of relevant target or inactive ligation.

The three probes were prepared on solid support without the need for post-synthesis modification. In the universal probe, the iodide and FAM-dU conjugate were introduced during standard DNA synthesis. The phosphorothioate group was introduced into the MUT and WT probes using standard sulfurization chemistry. The HEX dye was incorporated as a commercial phosphoramidite. The ROX dye was added to the terminus of the MUT probe by reaction of an activated ROX NHS ester derivative with a terminal amino group while the DNA remained on the solid support. Measurements were performed on a Spex Fluorolog-2 fluorimeter using a bandwidth of 1.8 nm and 1×1 cm quartz cuvettes. The source of radiation was a xenon arc lamp. All slits were set to 2 mm, resulting in approximately 3.4 nm resolution. Fluorescence measurements were taken in the right angle mode. Emission spectra were corrected for instrument response. FRET spectra were measured at FAM's excitation wavelength which is 495 nm.

Color-Based Detection of Ligation in Solution

The three labeled ALET probes were then incubated with 50 nucleotide single-stranded DNAs corresponding to wild-type or codon 12 mutant H-ras antisense strand. The reactions were followed by fluorescence spectrometer (FIG. 18). Results showed that after one hour of incubation with mutant DNA there was very little spectral change, but after 18 hours a significant FRET signal was observed, with quenching of the FAM signal coupled with gain in the ROX signal. An analogous result was observed with the same probe mixture in the presence of wild-type DNA, but with an increase in a yellow HEX signal. No increase in the 602 nm emission was observed in this second experiment, confirming that the WT probe effectively outcompetes the MUT probe for ligation to the universal probe. Although energy transfer and/or ligation appeared to be incomplete in both cases, difference spectra (comparing 1 hour to 18 hours, FIG. 18) allowed this background to be eliminated, and clearly showed the expected energy transfer signals. Significantly, the energy transfer did not occur until ligation brought the two dyes into permanent proximity, since simple hybridization of the probes was expected to be complete within seconds at these concentrations.

The products of these ligation reactions were also examined by denaturing gel electrophoresis, where the longer ligated probes were readily separated from any unreacted starting materials. These products were visualized over a UV transilluminator and digitally imaged. In the presence of mutant DNA the ligated probe appeared red to the eye, which indicates (1) that energy transfer within the ligated probe was efficient, and (2) that ligation of the mismatched WT (HEX) probe occurred to a very small extent if at all. In a second experiment, the same probes were incubated instead with wild type DNA. Results in this case were quite distinct, giving a clearly yellow ligation product having slightly slower mobility, presumably because of the difference in dye structure. None of this retarded yellow band was observable in the mutant DNA ligation. In subsequent ligations the MUT/universal probe pair was used in increasing dilutions with wild type DNA. The red MUT signal appeared to dilute as expected, with no yellow-tagged product visible, suggesting that unintended ligation occurs to very little extent.

Discussion

The phosphorothioate-iodide autoligation chemistry is thus shown to proceed efficiently on RNAs as well as DNAs, and we have developed a three probe strategy coupled to a color change as a reporting system. When products can be separated from reactants, such as in blot or gel based assays, then simple radiolabeling can be used for detection with autoligating probes. In that case, one must probe for a single sequences at a time. The ALET probe strategy, however, allows the ligation reaction to be followed visually or spectroscopically. Since more than one acceptor dye can be used, this makes it possible to use more than one mutation probe simultaneously. Two were used in the present case, although it is possible that more than two could be used with careful choice of FRET donor with multiple acceptors.

The observation of turnover on the DNA target is interesting and potentially useful, as it results in significant amplification of the ligation signal. The observation of higher turnover at the lowest target concentration is expected in a case of product inhibition, as no doubt occurs here. It is expected that even lower target concentrations would lead to higher degrees of turnover, as the concentration of the duplex product necessarily drops. It is also possible that alteration of the ligation chemistry might result higher degrees of turnover by lowering duplex stability more than pre-ligation complex stability. For example, incorporation of a phosphorylacetylamino bond as in Letsinger et al. (U.S. Pat. No. 5,476,930), which approximates the natural phosphodiester linkage less closely than a phosphorothioester or a phosphoroselenoester linkage, might increase turnover on the DNA target. Alternatively, use of a 5'-deoxy-5'-iodomethylene-2'-deoxynucleoside on the 5' end of the upstream oligonucleotide probe might likewise destabilize the hybridization with the target and increase turnover.

One of the most useful features of the autoligation chemistry is its ability to be utilized in the direct detection of RNAs. We are unaware of any other ligation-based genetic detection method in which this capability has been demonstrated. At present, RNAs are commonly detected by simple hybridization, such as in Northern blots and in situ hybridization, or are detected indirectly as their cDNAs after RT-PCR amplification. The present method offers considerably higher sequence specificity than simple hybridization alone, and the ALET probes allow for ease of detection by changes in fluorescence emission. These probes can be used with no more difficulty than simple hybridization probes, since no extra reagents or enzymes are needed. Indeed, unreacted probes are more easily washed from targets (such as in blots) because of their very short length. In addition, the ALET probe strategy allows unreacted probes to be easily distinguished from ligated (specifically hybridized) probes because of the change in emission wavelength on ligation. Although multiple dyes are used in this approach, only one excitation source is required (as in ET primers; S. Hung et al., Anal. Biochem. 252:78–88 (1997)) because only one donor label is used. A possible limitation in this autoligation strategy is that the current reagents allow only for ligations in which the downstream probe has a "T" at its 5' end (and thus the target has an "A" at this position). Nevertheless, there is a simple answer to this problem: one could utilize a 5'-iodoC variant of the 5'-iodoT used here. While not commercially available at present, we anticipate that it could be readily produced (see Example VI).

Ligase enzymes have been used recently in a related fluorescent reporter probe strategy, giving color-based FRET signals (M. Samiotaki et al., Genomics 20:238–42 (1994)). However, ligases, while highly sequence specific, require significantly longer probes than the 7mers used here. Longer probes would likely remain bound even prior to ligation, thus rendering the FRET responsive to binding rather than ligation and necessitating dissociation of the oligonucleotide probes or ligation product from the template polynucleotide before ligation can actually be detected. In addition, the use of longer sequences requires higher stringency to wash away unligated probes. A second potential difficulty with the use of ligase enzymes in this approach is that efficient energy transfer as we observe here requires close dye proximity, and it is questionable whether ligases (which are highly sensitive to native DNA structure), would accept probes with dye labels positioned within the ligase binding site. Third, as already mentioned, ligase enzymes would not allow detection of RNA as do ALET probes. Finally, the autoligating probes are simpler to use because they do not need added

Example V

Rapid and Selective Selenium-Mediated Autoligation of DNA Strands

Introduction

This Example describes a convenient and efficient new chemistry for the joining of DNA ends, and its use in detection of RNA and DNA sequences. This autoligation approach involves the reaction of a phosphoroselenoate anion on one strand with a 5'-carbon carrying an iodide leaving group on another. Selenium has previously been incorporated into DNA at non-bridging 25 positions in the phosphodiester linkage (K. Mori et al., Nucleic Acids Res. 17, 8207–8219 (1989)); however, the monosubstituted selenium was unstable and was rapidly lost. Prior to the present work, bridging selenium esters were unknown in nucleic acids.

Thus the objectives of this study were to test (i) whether the phosphoroselenoate anion would be stable enough in solution for utility in ligations; (ii) whether the intended ligation reaction would occur and at what rate; (iii) whether the product (a bridging phosphoroselenoate ester embedded in a longer DNA strand) would be hydrolytically stable; and (iv) how well this selenium-bridged DNA hybridizes with complementary nucleic acids.

Oligonucleotide Synthesis

All oligodeoxynucleotides were synthesized on 1 µmole scale on an ABI model 392 synthesizer using standard β-cyanoethylphosphoramidite coupling chemistry. Deprotection and removal of iodine-containing strands from the CPG support was done by incubation in concentrated ammonia for 24 hours at 23° C. to avoid small amounts of degradation which occur at 55° C. Automated RNA synthesis was carried out using t-butyldimethylsilyl-protected phosphoramidites from Glen Research. Oligonucleotides were deprotected in 3:1 concentrated ammonia: ethanol at 55° C. for 18 hours and dried. Silyl protecting groups were removed by adding 400 µL 1M tetrabutylammonium fluoride in tetrahydrofuran (Sigma) to the residue and shaking at room temperature for 24 hours. RNA was desalted on a Sep-pak column (Water) and purified by denaturing polyacrylamide gel electrophoresis. Purification of target oligodeoxynucleotides was carried out by preparative denaturing polyacrylamide gel electrophoresis. All DNAs and RNAs were quantitated by UV absorbance using the nearest neighbor approximation to calculate molar absorptivities.

Incorporation of Selenium

Oligonucleotides containing 3' phosphoroselenoate groups were prepared as for 3' phosphate groups, but with selenizing reagents replacing the standard oxidation step. Typically, the synthesis was initiated using Phosphate-ON controlled pore glass (Glen Research). Detritylation was followed by coupling with the 3' end nucleotide (in this case, using G phosphoramidite (Applied Biosystems)). Prior to the next step (oxidation), the synthesis was stopped. The selenization reaction was carried out manually, by removing the synthesis column from the synthesizer. Two selenizing reagents were tried: a solution of 0.1M KSeCN (Aldrich) in $CH_3CN$ (N. Seeman, Annu. Rev. Biophys. Biomol. Struct, 27, 225–248 (1998)). and a suspension of 0.1M Se powder (Aldrich) in dioxane (W. Stec et al., J. Am. Chem. Soc., 106, 6077–6079 (1984)). Both were purged with nitrogen for one hour to remove oxygen. $0.1M$ $KSeCN/CH_3CN$ was found to give a higher degree of selenium incorporation. The controlled pore glass beads were transferred from the DNA synthesis column to a screw-cap vial. The vial was filled with the selenizing reagent, and shaken at room temperature for 20 hours. Beads were recovered by filtering through glass wool. After washing with $CH_3CN$, beads were put back into the DNA synthesis column and the rest of the chain elongation was carried out in the normal fashion. Deprotection and cleavage from the support was carried out in concentrated ammonia for 24 hr at 23° C. The deprotection solutions were lyophilized to a pellet, and the oligonucleotides were used without further manipulation.

Synthesis of 5'-iodinated Oligonucleotides

Oligodeoxyribonucleotides were synthesized on an Applied Biosystems (ABI) 392 synthesizer using standard β-cyanoethylphosphoramidite chemistry. 5' Iodo-oligonucleotides were synthesized by the standard coupling protocol using a 5'-iodo-T phosphoramidite from Glen Research (Examples I and II). Deprotection and removal of iodine-containing strands from the CPG support was done by incubation in concentrated ammonia for 24 hours at 23° C. to avoid small amounts of degradation that occur at 55° C. Oligonucleotides were used without further manipulation after lyophilization. They were quantitated by the nearest neighbor method. Iodo-T was treated as unmodified T in these calculations.

Ligation Reactions

Ligations were performed in 600 µl pH 7.0 Tris-borate (70 mM) buffer containing 10 mM $MgCl_2$, with target and probe DNA concentrations of 1.3 µM. Ligations also contained 50 µM dithiothreitol. Reactions were incubated at 37° C. Aliquots (100 µL) were removed at various times and then were frozen and lyophilized for one hour. Pellets were taken up in 5 µL water-formamide-urea loading buffer. Samples were heated to 95° C. for 2 minutes and then chilled on ice prior to loading on 20% polyacrylamide gels containing 8 M urea. Gels were visualized with Stains-All dye (Sigma) and quantified by densitometry using NIH Image version 1.62b7 software.

In cases that were followed quantitatively, a fluorescent-labeled iodinated oligonucleotide (as in FIG. 19, but with fluorescein-dT (Glen Research) replacing T at the 3rd position) was used. Fluorescence images of gels were obtained using a Molecular Dynamics Storm 860 Fluorimager, and ligated starting material and product bands were quantitated with ImageQuant (Version 1.2). FIG. 21 shows the time course of ligation of 7mer and 13mer probes on a DNA template using phosphoroselenoate or phosphorothioate as nucleophile. The 13mer probe is labeled with fluorescein, and fluorescence is imaged on a Molecular Dynamics 860 Phosphorimager/Fluorimager. The lane at far right shows extent of ligation of mutant probes on the singly mismatched wild-type DNA target after 1440 minutes. In some cases, ligation products were isolated by preparative denaturing polyacrylamide gel electrophoresis. Bands were visualized by UV shadowing, and were excised from the gel. The crushed gel was incubated with 0.1 N NaCl and the DNA solution was separated from the gel by centrifugal filtration. The DNAs were desalted by dialysis against water.

Ligated oligonucleotides were characterized by their gel mobility and by electrospray mass spectrometry:

```
5'dGTG GGC GCC G-pO-TC GGT GT    (SEQ ID NO: 9)
``` calculated mass 5274.6; found, 5274

```
5'dGTG GGC GCC G-pS-TC GGT GT    (SEQ ID NO: 10)
``` calculated mass 5290.6; found, 5290

```
5'dGTG GGC GCC G-pSe-TC GGT GT   (SEQ ID NO: 11)
``` calculated mass 5337.6; found, 5337

Thermal Denaturation Studies

Solutions for thermal denaturation studies contained a 1:1 ratio of the complementary strands shown below (1.0 µM each). Also present was 10 mM $MgCl_2$ buffered with 10 mM Na.PIPES at pH 7.0. Solutions were heated to 90° C. and allowed to cool slowly to room temperature prior to the melting experiments.

Melting studies were carried out in Teflon-stoppered 1 cm path length quartz cells under a nitrogen atmosphere on a Varian Cary 1 UV-VIS spectrophotometer equipped with a thermoprogrammer. Absorbance was monitored at 260 nm while the temperature was raised from 10° C. to 90° C. at a rate of 0.5° C./min. Melting temperatures were determined by computer fitting using program Meltwin 3.0 assuming a two state model.

Hydrolysis Studies

Oligonucleotides were incubated in Tris.HCl buffers (10 mM) at the indicated pH at 23° C. The DNA concentration was 25 µM. After 7 days, 5 µL aliquots were removed and added to 5 µL water-formamide-urea loading buffer. Samples were heated t 95° C. for 2 minutes and then chilled on ice prior to loading on a 20% polyacrylamide gel containing 8 M urea. Gels were visualized with Stains-All dye (Sigma).

Results and Discussion

We incorporated selenium into short synthetic DNA strands by methods analogous to those commonly used for sulfur (e.g., S. Beaucage et al., Tetrahedron, 48, 2223–2311 (1992). We found KSeCN to be more convenient as a selenizing reagent than Se powder, and experimentation showed that the reaction could be carried out on the glass beads after temporary removal from the synthesizer. The presence of the selenium did not noticeably affect the subsequent phosphoramidite coupling yields. The end-selenated oligonucleotides were removed from the solid support and deprotected using standard ammonia conditions. Because of uncertainties as to the long-term stability of the terminal phosphoroselenoate anion, we used this modified DNA without further purification in subsequent ligation reactions. For reaction with this nucleophile we prepared 5'-iodinated oligonucleotides by incorporation of 5'-iodothymidine phosphoramidite, as described in Examples I and II.

As with other DNA ligations, this chemistry requires that the reacting ends be bound at adjacent sites on a longer complementary template strand, which serves to raise effective concentrations of the reactive groups markedly. Ligations were therefore carried out in the presence of fully complementary DNA or RNA template strands. The sequences chosen for the studies were taken from the H-ras protooncogene (the target sequence "WT") and the activated H-ras oncogene (labeled "MUT"), which has a C->A point mutation in codon 12 (FIG. 19). We used a 13mer iodinated probe that was fully complementary both to normal and oncogene sequences. Combined with this were used either of two shorter (7mer) selenium-containing probes, one complementary to the normal codon 12 and the other to the mutant sequence. The reactions were carried out at 1.3 µM DNA concentration in a pH 7.0 Tris-borate buffer containing 10 mM $MgCl_2$, and were quantitated by fluorescence imaging of gels separating ligated products.

Experiments showed that on the DNA target, the selenium chemistry proceeds more rapidly than the older sulfur chemistry (FIG. 20). Analysis of the initial slopes of product yields as a function of time shows a difference of 3.7-fold in rate when MUT probes were used on the MUT target DNA. Similarly, we carried out the same reaction on the MUT target RNA, and we again found that the selenium chemistry proceeded more rapidly (a 3.5-fold difference).

Importantly, we found that the selenium/iodide autoligation was highly sensitive to the sequence of the target nucleic acid. We carried out a ligation reaction using the 13mer iodo-probe with the 7mer MUT selenium-containing probe and followed the course of the reaction with fully complementary (MUT) or singly mismatched (WT) DNAs. The mismatch in the latter case is T-C. While the fully complementary ligation proceeded to 27% yield in 60 minutes, the mismatched case showed no ligated product at this short time. After 24 hours, we were able to detect a trace of ligation product; quantitation of this product suggests a 190-fold slower rate for ligation based on the initial slopes. Thus the selenium ligation is highly sensitive to a single base mismatch. This is greater selectivity than reported for T4 DNA ligase, the enzyme most widely used for ligations.

Because bridging selenium esters were previously unknown in DNA, we characterized the product, a 5' bridging phosphoroselenoester, produced in an autoligation reaction. Electrospray mass spectrometry confirmed the presence of the selenium in a 17mer DNA strand, clearly distinguishing it from sulfur- and oxygen-containing strands of the same sequence. The hydrolytic stability of this joined DNA was also tested, by a seven-day incubation at 23° C. in buffers over the pH range 5–9. We found no measurable degradation at any of these pH values, indicating that the bridging ester has good stability. Based on these data, we place a lower limit of at least one year on the half-life for hydrolysis of this junction under these conditions.

In a related experiment, the ALET probe strategy of Example IV was successfully adapted to the selenium-mediated ligation, and ligation was detectable by way of fluorescence resonance energy transfer.

Finally, we tested the ability of the selenium-bridged DNA to hybridize to a complementary strand of DNA. For comparison we evaluated sulfur-bridged DNA and natural DNA having the same sequence. Binding stability of the resulting duplexes were measured by thermal denaturation experiments in pH 7 buffer containing 10 mM $Mg^{2+}$. The results showed that the selenium-bridged DNA hybridizes somewhat less strongly than the natural oxygen-containing case, with $T_m$ values (free energies (70° C.)) of 73° C. (−11.3 kcal/mol) for selenium and 76° C. (−13.1 kcal/mol) for oxygen. Perhaps not surprisingly, the sulfur case falls between the two at 74° C. (−12.0 kcal/mol). Overall, the selenium does not appear to be strongly destabilizing to the double helix.

In Examples III and IV we showed that a sulfur-mediated autoligation reaction can be employed in sequence-sensitive detection of nucleic acids in solution. The results in this Example show that the use of selenium as a nucleophile allows for a substantial increase in ligation rate, and that the chemistry is carried out with equal ease. Importantly, the selenium reaction can be carried out on RNA strands as readily as DNA strands and shows very high selectivity against point mutations. It is notable that enzyme-mediated ligations are widely used in diagnostic sensing of DNA sequences, but cannot be used for RNA analysis. Thus, the selenium autoligation may prove useful in diagnostic strategies for direct analysis of RNAs. Because the newer selenium-mediated reaction is faster, we anticipate that it may prove more convenient than previous sulfur chemistry.

The selenium/iodide autoligation reaction may also find utility in a number of other applications for which previous ligation chemistries may not be well suited. For example, the selenium may be employed for probing mechanisms of catalyzed nucleic acid hydrolysis, which seems plausible given that sulfur substitution is widely used for this kind of study. In addition, 25 selenium incorporation in DNAs may find use in structural biology, since heavy atom replacement is widely used as an aid in solving complex x-ray crystal structures of large biomolecules and complexes. It has not previously been possible to stably incorporate selenium into DNA, in analogy to the use of selenomethionine in proteins (see, e.g., I. Uson et al., Curr. Opin. Struct. Biol., 9, 643–648 (1999)).

Example VI

Synthesis of Various 5'-Iodo-2'-deoxynucleosides

Base-Protected Derivatives of
5'-iodo-5'deoxy-2'-deoxycytidine

Using the standard transient protection strategy, 2'-deoxycytidine was treated in pyridine first with trimethylsilyl chloride and then benzoyl chloride to protect the N4-amino group as the benzoyl derivative, which was purified by silica gel chromatography. The base-protected nucleoside was then treated with Moffat's reagent (methyltriphenoxyphosphonium iodide) in tetrahydrofuran solvent to yield the protected 5'-iodo-5'-deoxy-2'-deoxycytidine in moderate yield. It was purified by silica gel chromatography.

To prepare this nucleoside for DNA synthesis, the 3'-O-phosphoramidite derivative is prepared by reacting the iodonucleoside with 2-cyanoethyldiisopropylaminophosphonamidic chloride in the presence of diisopropylethylamine. The product is isolated by silica gel chromatography.

Base-Protected Derivatives of 5'-iodo-5'deoxy-2'-deoxyadenosine

Using the standard transient protection strategy, 2'-deoxycytidine was treated in pyridine first with trimethylsilyl chloride and then benzoyl chloride to protect the N6-amino group as the benzoyl derivative, which was purified by silica gel chromatography. The base-protected nucleoside was then treated with Moffat's reagent in tetrahydrofuran solvent to yield the 5'-iodo-5'-deoxy-2'-deoxyadenosine derivative in moderate yield. It was purified by silica gel chromatography.

To prepare this nucleoside for DNA synthesis, the 3'-O-phosphoramidite derivative is prepared by reacting the iodonucleoside with 2-cyanoethyldiisopropylaminophosphonamidic chloride in the presence of diisopropylethylamine. The product is isolated by silica gel chromatography.

Base-Protected Derivatives of 5'-iodo-5'deoxy-2'-deoxyguanosine

Using the standard transient protection strategy, 2'-deoxycytidine was treated in pyridine first with trimethylsilyl chloride and then isobutyric anhydride to protect the N2-amino group as the isobutyryl derivative, which was purified by silica gel chromatography. The base-protected nucleoside was then treated with Moffat's reagent in tetrahydrofuran solvent to yield the 5'-iodo-5'-deoxy-2'-deoxyguanosine derivative in moderate yield. It was purified by silica gel chromatography.

To prepare this nucleoside for DNA synthesis, the 3'-O-phosphoramidite derivative is prepared by reacting the iodonucleoside with 2-cyanoethyldiisopropylaminophosphonamidic chloride in the presence of diisopropylethylamine. The product is isolated by silica gel chromatography.

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for detecting a genetic polymorphism in a target nucleic acid comprising:
providing a mutant polymorphism oligonucleotide probe that is complementary to a region on the target nucleic acid that comprises the genetic polymorphism;
providing a universal oligonucleotide probe capable of binding to the target nucleic acid at a region that is conserved in the analogous wild-type nucleic acid;
wherein one oligonucleotide probe constitutes an upstream oligonucleotide having, as its 5'-end, a ribo- or deoxyribonucleoside wherein the 5'-hydroxyl group thereof has been replaced by a leaving group, and the other oligonucleotide probe constitutes a downstream oligonucleotide comprising, at its 3' end, a nucleoside comprising a 3' functional group selected from the group consisting of 3'-phosphoroselenoates such that, when both probes are bound to the target nucleic acid, an end of the universal oligonucleotide probe is substantially adjacent to an end of the mutant polymorphism oligonucleotide probe so as to position the 5' leaving group and the 3'-functional group in close proximity to one another;
contacting the target nucleic acid with the universal oligonucleotide probe and the mutant polymorphism oligonucleotide probe to yield an autoligated oligonucleotide product comprising the universal oligonucleotide probe and the mutant polymorphism probe; and
detecting the presence of the autoligated oligonucleotide product, wherein the presence of an autoligated product indicates the presence of a genetic polymorphism in the target nucleic acid.

2. The method of claims 1 wherein at least one of the mutant polymorphism oligonucleotide probe and the universal oligonucleotide probe further comprises a detectable label.

3. The method of claim 2 wherein the detectable label is a radiolabel.

4. The method of claim 1 wherein the genetic polymorphism is selected from the group consisting of a single base mutation, a plurality of single base mutations, a deletion, an insertion, and a genetic rearrangement.

5. The method of claim 1 wherein the nucleotide position is not the nucleotide position corresponding to the ligation junction end of the mutant polymorphism probe.

6. The method of claim 1 wherein the target nucleic acid is DNA.

7. The method of claim 1 wherein the target nucleic acid is RNA.

* * * * *